United States Patent
Cane et al.

(10) Patent No.: US 7,647,085 B2
(45) Date of Patent: *Jan. 12, 2010

(54) METHOD OF AND APPARATUS FOR INVESTIGATING TISSUE HISTOLOGY

(75) Inventors: Michael Roger Cane, Royston (GB); Michael Andrew Beadman, Royston (GB); Symon D'Oyly Cotton, Great Gransden (GB)

(73) Assignee: Astron Clinica Limted, Toft (GB)

(*) Notice: Subject to any disclaimer, the term of this patent is extended or adjusted under 35 U.S.C. 154(b) by 840 days.

This patent is subject to a terminal disclaimer.

(21) Appl. No.: 11/151,389

(22) Filed: Jun. 13, 2005

(65) Prior Publication Data

US 2005/0251049 A1 Nov. 10, 2005

Related U.S. Application Data

(63) Continuation of application No. 09/760,387, filed on Jan. 12, 2001, now Pat. No. 7,054,674, which is a continuation-in-part of application No. 09/314,751, filed on May 19, 1999, now Pat. No. 6,324,417.

(30) Foreign Application Priority Data

| Nov. 19, 1996 | (GB) | ............................ 9624003.1 |
| Nov. 19, 1997 | (WO) | ............... PCT/GB97/03177 |
| Jun. 4, 1999 | (GB) | ............................ 9912908.2 |
| Oct. 28, 1999 | (GB) | ............................ 9925414.6 |
| Jun. 1, 2000 | (WO) | ............... PCT/GB00/02124 |

(51) Int. Cl.
 *A61B 5/05* (2006.01)
(52) U.S. Cl. .................. 600/410; 600/407; 382/128
(58) Field of Classification Search ............. 600/407, 600/473, 475–478, 410; 382/128
See application file for complete search history.

(56) References Cited

U.S. PATENT DOCUMENTS 5,079,698 A 1/1992 Grenier et al.

(Continued)

FOREIGN PATENT DOCUMENTS

CA 2196187 2/1996

(Continued)

OTHER PUBLICATIONS

Symon D'O Cottin in "Do all human skin colours like on a defined surface within LMS space?", University of Birmingham Technical Report, Dec. 30, 1995.

(Continued)

*Primary Examiner*—Brian Casler
*Assistant Examiner*—Nasir Shahrestani
(74) *Attorney, Agent, or Firm*—Oliff & Berridge, PLC

(57) ABSTRACT

Apparatus for monitoring the presence of one or more chromophores in a tissue sample, comprises a light source for projecting light to illuminate an area of such tissue sample, a photo-receptor for receiving light remitted by the illuminated area of tissue, and spectroscopic analyzer means for monitoring the remitted light, a comparator having means for comparing variations in the intensity and spectral characteristics of the remitted light with respect to the intensity and spectral characteristics of the projected light at different wavelengths and with a record of the intensity and spectral characteristics of light remitted by a reference sample of such tissue and means for emitting a control signal in response to any such variations. Methods of analyzing tissue histology, especially skin histology, are discussed, and a mathematical model is proposed for the analysis and comparison of the remitted light with a reference sample.

39 Claims, 9 Drawing Sheets

U.S. PATENT DOCUMENTS

| | | | |
|---|---|---|---|
| 5,353,790 A | 10/1994 | Jacques et al. | |
| 5,440,388 A | 8/1995 | Erickson | |
| 5,555,885 A | 9/1996 | Chance | |
| 5,735,276 A | 4/1998 | Lemelson | |
| 5,784,162 A | 7/1998 | Cabib et al. | |
| 5,986,770 A | 11/1999 | Hein et al. | |
| 6,081,612 A | 6/2000 | Gutkowicz-Krusin et al. | |
| 7,054,674 B2 * | 5/2006 | Cane et al. | 600/407 |

FOREIGN PATENT DOCUMENTS

| | | |
|---|---|---|
| WO | WO 90/13091 | 11/1990 |
| WO | WO 94/16622 | 8/1994 |
| WO | WO 96/14795 | 5/1996 |

OTHER PUBLICATIONS

Clark et al., "The Histogenesis and Biologic Behaviour of Primary Human Malignant Melanomas of the Skin", Cancer Research 29, 705-729, Mar. 1969.

CD Neville, "Melanoma: Issues of Importance to the Clinician", British Journal of Hospital Medicine, Mar. 1985.

SL Jacques, "The Role of Skin Optics in Diagnostic and Therapeutic Uses of Lasers," Lasers in Dermatology, 1991, pp. 1-21-, XP000607863.

Kini Dhawan, "Three-Dimensional Imaging and Reconstruction of Skin Lesions," Comput Med Imaging Graph 1992, May-June; 16(3): 153-61.

* cited by examiner

METHOD OF AND APPARATUS FOR INVESTIGATING TISSUE HISTOLOGY

CROSS REFERENCE TO RELATED APPLICATIONS

This application is a continuation of U.S. application Ser. No. 09/760,387, filed Jan. 12, 2001, which issued on May 30, 2006 as U.S. Pat. No. 7,054,674, which, in turn, is a Continuation-In-Part of prior application Ser. No. 09/314,751, filed May 19, 1999, which issued on Nov. 27, 2001 as U.S. Pat. No. 6,324,417, both of which are incorporated herein by reference.

This invention relates to a method of and apparatus for the investigation of tissue histology. The invention has particular reference to the investigation of chromophores within layers close to the surface of such tissue, and while the invention may be applied in the investigation of laboratory tissue specimens, whether obtained from a biopsy or necropsy, it was developed with the particular intention of enabling in vivo observation of a subject without the need for any surgical intervention which might expose the subject, or indeed the surgeon, to the risk of infection. The invention is thus applicable especially to the investigation of epithelial tissue, such as the skin and linings of the respiratory and digestive tracts and other surfaces to which visual access may be had, such as the retina, without removing the tissue being investigated from the body of the subject. The invention is particularly applicable to the non-invasive investigation of tissue histology.

In order to appreciate the presence of abnormalities in the tissue being examined it is first necessary to have an appreciation of the structure of normal tissue of that type.

Though the invention may be adapted for the investigation of other animal tissue, it was originally developed with particular regard to the investigation of conditions whose symptoms include abnormalities in the human skin, and it is in that context that it will be particularly explained.

Thus, in order to appreciate the presence of abnormalities in the skin it is first necessary to have an appreciation of the structure of normal skin.

The presence and extent, including depth and concentration, of chromophores within epithelial tissue such as the skin is considered to be an important indicator of a variety of ailments and other conditions. The invention is considered to be potentially useful for the preliminary screening of patients to identify those who should be referred to an appropriate clinician for diagnosis and further to assist the clinician in diagnosis and in some embodiments to indicate whether a given treatment would be of value to the patient, and for other purposes.

The skin is divided into two main layers, the epidermis and the dermis, each of which is itself divided into several sub-layers. Starting from the deepest layer, the subcutaneous layer is overlain by a reticular layer of the dermis which is composed of coarse and dense interlacing bundles of collagen fibers ("type 1 collagen") which are intermingled with reticular fibers and elastic fibers. Over this is the papillary dermal layer which is also composed of collagen fibers but these are much finer than those of the reticular layer in that they are not bundled together. The collagen in the papillary dermis is mainly "type 3 collagen", and it constitutes connective tissue joining the epidermis and the reticular layer of the dermis. The dermis is also rich in blood vessels. The papillary dermis is located immediately beneath the epidermis and is separated from it by the basal lamina. The dermo-epidermal junction is highly irregular in profile due to dermal papillae projecting up from the dermis between rete ridges or pegs projecting down from the epidermis. It is the presence of these rete ridges or pegs and papillae which gives the skin elasticity, and their interaction also provides an anchor for the epidermis. Epithelium cells multiply continuously in a germinative layer, just above the basal lamina, to replace cells lost from the surface of the epidermis. The germinative layer, which is fed by blood vessels leading through the dermis, also contains melanocytes for the production of melanin. The epithelium cells from the germinative layer move upwards into the layer above, the spinous layer, and thence into the granular layer where the cells contain granules which are involved in the formation of keratin. It is in this granular layer that the cells of the epidermis die. Above the granular layer, is a clear and translucent layer and above that is the outermost layer, the cornified layer. This is composed of clear dead scale-like skin which is progressively lost from the surface by exfoliation.

Historically, dermatological investigations have taken place by biopsy, that is by surgical removal of samples of skin tissue followed by microscopic examination of thin sections of the skin tissue usually viewed at right angles to the skin surface. The information obtained is limited in area to the thin section, unless a number of sections is examined. Each section requires to be cut, stained and mounted onto a microscope slide, and they are therefore time consuming to prepare. Further the technique is invasive, and there may be a consequent risk of infection either at the biopsy site or from the biopsied material, or both, unless stringent precautions are taken.

In normal circumstances, the healthy epidermis is translucent and transmits light diffusely; a proportion of incident light will be absorbed in the epidermis, depending in part on the amount of melanin present in the epidermis, and a proportion will be transmitted through to the dermis. Because the papillary dermis largely consists of type 3 collagen, that is, a very fine network of collagen fibers (as low as 2 µm in diameter), light passing through the papillary dermis will be subject to Rayleigh scattering. A proportion of the incident light will be scattered inwards and a proportion will be back-scattered, and some of this scattered light will be remitted back through the epidermis. In the reticular dermis the fibers are of type 1 collagen, that is, they are clumped or bundled together, and they are largely parallel to the skin surface: thus they are too coarse to give rise to Rayleigh scattering, and light penetrating to the reticular dermis will continue until absorbed or deflected by some discontinuity.

Thus light remitted by the epidermis will have its spectral characteristics altered by the effects of melanin, blood and other chromophores in the skin.

The mean thickness of the papillary dermis can vary quite considerably as between one part of the body and another, for example, and in particular, the height and population density of dermal papillae tends to increase according to the stress to which a particular area of skin is habitually subjected. Thus, the thickness of the papillary dermis over a joint will tend to be greater than that over a relatively non-stressed region such as the lower back. These variations, and variations between different subjects will have a marked effect on the skin color, but we have found that it is possible to construct a mathematical model which allows corrections to be made for this effect. When so corrected it is notable that the color of normal healthy human skin lies in a well defined surface area within a particular color space, for example the CIE LMS color space. That surface area encompasses all colors of normal healthy human skin irrespective of the amount of melanin within the skin and thus irrespective of race or degree of tanning. This approach allows parameters relating to chromophores within the skin to be measured in a more accurate and repeatable way through optical means than was permitted by previously existing techniques.

According to the present invention, there is provided a method of monitoring the presence of one or more chromophores in a sample of biological tissue, which method comprises illuminating an area of such tissue sample by projecting light from a light source, receiving light remitted by the illuminated area of tissue at a photo-receptor, spectroscopically analyzing the remitted light, and comparing variations in the intensity and spectral characteristics of the remitted light with respect to the intensity and spectral characteristics of the projected light and with data representing a datum sample of intensity and spectral characteristics, and emitting a control signal in response to any such variations.

In some embodiments, the invention is applied for the endoscopic monitoring of the presence of one or more said chromophores in the tissue sample, but the invention is particularly apt for a wholly non-invasive analysis of tissue structure.

The invention in particular includes a method of non-invasively analyzing tissue structure, comprising the steps of:

(i) measuring red or infrared radiation from at least one location in an area of tissue under investigation so as to give an indication of any layered structure in said area;

(ii) measuring the tissue color co-ordinates at said at least one location in said area of tissue;

(iii) using data obtained in measuring steps (i) and (ii) to calculate corrected tissue color co-ordinates in respect of the or at least one said area which corresponds to a predetermined thickness of said layered structure, and;

(iv) comparing the corrected tissue color co-ordinates obtained in step (iii) with a reference color co-ordinate range for healthy tissue having a layered structure of the same predetermined thickness.

Such method may be used for locating and measuring the properties of an abnormality in a layered structure, for example a collagen-rich layer, such as skin. The light measured in step (i) above suitably extends across the UV and/or visible and/or IR regions.

Such method most preferably further comprises the additional step of;

(v) identifying corrected tissue color co-ordinates which lie outside the reference color co-ordinate range.

Such method also preferably further comprises the additional steps of;

(vi) comparing the degree of deviation of the corrected tissue color co-ordinates which lie outside the reference color co-ordinate range with generalized levels of deviation from a reference color co-ordinate range known to be associated with differing abnormalities in said tissue, and;

(vii) using the tissue color co-ordinates to assess the degree of abnormality of said tissue.

In alternative preferred embodiments, the method comprises the additional steps of (vi) calibrating the corrected tissue color co-ordinates with the corrected tissue co-ordinates of at least one tissue location having color co-ordinates lying within said reference color co-ordinate range for normal tissue;

(vii) using the tissue color co-ordinates to assess the degree of abnormality of said tissue.

Suitably, said calibration in step (vi) includes estimating the level of epidermal melanin at said location by reference to epidermal melanin levels calculated within at least one normal skin region adjacent said location. Alternatively said calibration in step (vi) may include measuring epidermal melanin levels at said location by assessing the deviation at the blue end of the spectrum at said location from the reference color co-ordinate range for normal skin.

The invention further includes a method of mapping the papillary surface of an area of the dermis which comprises illuminating the surface of the skin over that area with light and monitoring the intensity of the light remitted from along at least one line or sequence of points, the light having a wavelength sufficiently far into the infra-red that its absorption by melanin and blood is negligible, or having at least two wavelengths of which at least one is in excess of 600 nm and deriving therefrom a theoretical intensity of remitted light which is independent of the presence of melanin or blood, and from the remitted light intensity deriving a signal corresponding to the concentration of collagen within the papillary dermis along the or each line or at each point, and producing a contoured image in which the apparent elevation of any point is dependent upon the strength of such signal.

The invention extends to apparatus which may be used for performing a method as herein defined, and accordingly includes apparatus for monitoring the presence of one or more chromophores in a biological tissue sample, which apparatus comprises a light source for projecting light to illuminate an area of such tissue sample, a photo-receptor for receiving light remitted by the illuminated area of tissue, and a spectroscopic analyzer for monitoring the remitted light, a comparator for comparing variations in the intensity and spectral characteristics of the remitted light with respect to the intensity and spectral characteristics of the projected light at different wavelengths and with data representing a datum sample of intensity and spectral characteristics of light and a signal emitter for emitting a control signal in response to any such variations.

The invention extends to apparatus for non-invasively analyzing skin structure, comprising:

means for projecting UV and/or visible and/or red and/or infrared radiation onto an area of skin under investigation, measuring means for measuring remitted red or infrared radiation from at least one location over said area of skin so as to give an indication of the collagen thickness in said area;

skin color co-ordinate measuring means for measuring the skin color co-ordinates at said at least one location in said area of skin;

calculating means for using data obtained in measuring steps (i) and (ii) to calculate corrected skin color co-ordinates in respect of the or at least one said area which corresponds to a predetermined amount of collagen, and;

color comparison means for comparing the corrected skin color co-ordinates obtained in step (iii) with a reference color co-ordinate range for skin with the same collagen content.

The invention further extends to apparatus for mapping the papillary surface of an area of the dermis which comprises a light source illuminating the surface of the skin over that area with light which either has a wavelength sufficiently far into the infra-red that its absorption by melanin and blood is negligible, or which has at least two wavelengths of which at least one is in excess of 600 nm, means for monitoring the intensity of the light remitted along at least one line or sequence of points, and deriving therefrom an intensity or theoretical intensity of remitted light which is independent of the presence of melanin or blood, and means for deriving a signal from the remitted light intensity corresponding to the concentration of collagen within the papillary dermis along the or each line or at each point, and for producing a contoured image in which the apparent elevation of any point is dependent upon the strength of such signal.

The present invention is based on the findings reported by Symon D'O Cotton in "Do all human skin colors lie on a defined surface within LMS space?", University of Birmingham Technical Report, 30 Dec. 1995. The disclosure of such Technical Report is included herein by reference. In this Technical Report, the relation between healthy skin and the color of the skin represented in LMS, a particular color space, is reported, and it discloses that, for healthy skin, the coloration, regardless of race or amount of tanning, lies on a defined curved surface within a three-dimensional color space. This, if used with a correct color measurement system, can measure and quantify the amount of melanin and blood and other chromophores at any particular point at which this measurement is made. If the skin is sampled as an image, then corresponding images showing the variation of blood and melanin across the skin can be obtained. In the above Technical Report, it is disclosed that melanin can sometimes penetrate into the dermis producing the characteristic hues of melanoma and that this melanocytic descent has been quantified by Clark et al ("The Histogenesis and Biological Behavior of Primary Human Malignant Melanomas of the Skin", Cancer Research, 29, 1989) into five levels of tumor invasion, in which level 1 corresponds to confinement within the epidermis, level 2 corresponds to invasion into the papillary dermis, etc. In an alternative system, the extent of tumor invasion in mm from the cornified layer is expressed as the Breslow thickness. The above Technical Report also acknowledges that, in the case of melanoma, CD Neville ("Melanoma: Issues of Importance to the Clinician", British Journal of Hospital Medicine, March 1985) discloses the existence of a strong relationship between this level of invasion and prognosis. However, the above Technical Report does not disclose in detail any method suitable for taking the necessary measurements.

The invention is presently believed to be of particular value in the monitoring of color variations in epithelial and sub-epithelial tissues, and it is accordingly preferred that said datum sample represents the intensity and spectral characteristics of light remitted by a sample of epithelial or epithelial and sub-epithelial tissue. In particular, the invention is useful for investigating skin tissue histology, and for this purpose, it is desirable that said datum sample represents the intensity and spectral characteristics of light remitted by a sample of skin. It is desirable that said datum sample represents the intensity and spectral characteristics of light remitted by a sample of tissue of known structure. Alternatively, or in addition, it is desirable that said datum sample represents the intensity and spectral characteristics of remitted light as calculated from a mathematical optical model of the tissue.

The apparatus and method of the present invention may be utilized for monitoring the presence of a wide variety of chromophores in the skin and in other biological tissue. It is possible to derive data relating to the presence, depth, and concentration of a wide range of chromophores, depending on measurements being made at particular wavelengths. These wavelengths may readily be selectable by light filters which may be substituted into the light path, or the analyzer may be constituted by a spectroscope. The filters may be broad band filters or narrow band filters as appropriate for the analysis to be undertaken.

Examples of particular chromophores whose presence may be monitored include: melanin, blood, haemoglobin, oxy-haemoglobin, bilirubin, tattoo pigments and dyestuffs, keratin, collagen and hair.

It is to be understood that using the method of the invention, it is possible to reconstruct a full 3D model of the architecture of the skin or other tissue which conveys information grossly comparable to that available through microscopical examination of biopsied tissue.

In particular, having regard to the examination of skin, it has been found that the papillary dermal skin thickness can change markedly with some skin lesions which are not otherwise of concern. This throws the coloration of the skin off the surface of predicted coloration and so can give rise to false measurements of the histology of such skin lesions. It is for this reason that papillary dermis thickness is usually measured first, and subsequent calculations are based on the skin color co-ordinates corrected to a predetermined papillary dermis thickness. Any arbitrary value for this thickness may be chosen, such as $2.0 \times 10^{-4}$ m which is the average value for healthy human skin.

The thickness of the papillary dermis may be obtained by utilizing a method which will be described below with reference to FIG. 1.

In a preferred embodiment, the reference color co-ordinate range for normal skin at the predetermined papillary dermis thickness is obtained as disclosed in the above-mentioned Technical Report as a curved surface lying within a three-dimensional color space, with one of the bounding axes relating to the amount of melanin within the epidermis and the other relating to the amount of blood within the dermis. When an area containing dermal melanin is located, i.e. points do not lie on the normal color surface, the epidermal melanin value within this area is estimated by either reference to the reference color co-ordinate range for normal skin within regions identified as normal, or by reference to the epidermal melanin levels calculated within normal regions adjacent to said area containing dermal melanin. This value is then used with the corrected color co-ordinates of the abnormal region at the same predetermined papillary dermis thickness to compute invasion depth and concentration of dermal melanin. The corrected skin color co-ordinates for the area of skin under investigation may be calibrated to values equivalent to zero epidermal melanin. Instead of using LMS color space, it is possible to use any other color space, for example, the RGB color space or a UV G IR color space.

The dermis contrasts strongly in structure to that of the epidermis, being highly vascular, containing many sensory receptors and being made largely from collagen fibers to provide the essential structure of the skin. Between the epidermis and the dermis, the junction presents an extremely uneven boundary with finger-like dermal protrusions called dermal papillae projecting towards the skin surface. The dermis can be split into two further histologically distinct layers, the papillary dermis and the reticular dermis within which the structure of the collagen fibers differs significantly. The papillary dermis is situated directly below the epidermis and within which the collagen exists as a fine network of fibers. This is in contrast with the reticular dermis where the collagen fibers are aggregated into thick bundles which are arranged nearly parallel to the skin surface. In the case of melanin invasion of the papillary dermis, there is a layer containing blood, melanin and collagen, a layer containing either blood and collagen or melanin and collagen, depending upon whether melanin has passed the blood layer; and a layer containing just collagen. The different thicknesses of these layers, the amount of blood and the concentration of dermal melanin along with the amount of melanin in the overlying epidermis affect the remitted light. This can be modeled by calculating the net effect of these three layers for the differing parameters outlined.

A mathematical model describing the optics of the skin has been described in the above mentioned Symon D'O Cotton's Technical Report, whose disclosure has been included herein by reference, and this model can be extended to predict coloration of skin containing dermal descent of melanin.

As can be seen from FIG. 2, there are now four distinct layers within the dermis which can combine to construct a simple model, 1) a layer within the upper papillary dermis containing no melanin, 2) a layer within the upper papillary dermis containing melanin, 3) a layer within the lower papillary dermis containing melanin, 4) a layer within the lower papillary dermis containing no melanin.

It should also be noted that the condition of melanin existing up to the dermo-epidermal junction is facilitated by allowing the thickness of layer 1 to be zero and likewise melanin can exist up to the papillary-reticular dermis boundary by setting the thickness of layer 4 to be zero.

In computing a model to predict this coloration it is useful to make note of the fact that, as discussed in section 2.1 of the Technical Report, the amount of back scatter due to melanin can be considered negligible. Therefore, in the same manner that it was possible to apply the Kubelka-Munk theory to the papillary dermis (section 3.2.2 of the Technical Report), to compute the coloration of sections of papillary dermis containing blood, where the back scattering component of blood was considered negligible, it is possible to compute the coloration of sections containing melanin. In this situation $\zeta(\lambda)$ (scattering coefficient) remains dependent only on wavelength whilst $\alpha$ (fraction of radiation absorbed per unit path length) becomes $\alpha(\lambda,\rho,\phi)$ where $\phi$ represents the density of dermal melanin within that layer. Further, following the proof given in equation (17) of the Technical Report, $\alpha(\lambda,\rho,\phi)$ can be shown to be the sum of $\alpha_{iv}(\lambda)$, $\alpha_b(\lambda)$ and $\alpha_m(\lambda)$, where $\alpha_m(\lambda)$ is the absorption coefficient of melanin. From the above it is possible to calculate R and T (diffuse radiation and transmission respectively). For simplicity of notation it is helpful to consider $R_1$ and $T_1$ where, $$R_1(\lambda,\rho,\phi,d_n) = R(\beta(k(\alpha(\lambda,\rho,\phi)),s(\zeta(\lambda))),K(k(\alpha(\lambda,\rho,\phi)),s(\zeta(\lambda))),d_n) \quad \text{Eqn. 1}$$

and $$T_1(\lambda,\rho,\phi,d_n) = T(\beta(k(\alpha(\lambda,\rho,\phi)),s(\zeta(\lambda))),K(k(\alpha(\lambda,\rho,\phi)),s(\zeta(\lambda))),d_n) \quad \text{Eqn. 2}$$

where $d_n$ is the layer thickness.

As was shown in section 3.2.3 of the Technical Report, two-layer systems can be combined to produce the total remitted and transmitted light for the dermis resulting in equation (20) of the Technical Report.

This can be simplified using the geometric series $$a + ar + ar^2 + ar^3 + \ldots = \frac{a}{1-r} \quad \text{if } -1 < r < 1 \quad \text{Equation 3}$$

to $$R_{1total}(\lambda, \rho_{ud}, \rho_{ld}, d_{ud}, d_{ld}) = R_{1ud}(\lambda, \rho_{ud}, d_{ud}) + \frac{T_{1ud}(\lambda, \rho_{ud}, d_{ud})^2 R_{1ld}(\lambda, \rho_{ld}, d_{ld})}{1 - R_{1ud}(\lambda, \rho_{ud}, d_{ud}) R_{1ld}(\lambda, \rho_{ld}, d_{ld})} \quad \text{Eqn 4}$$

Similarly, $T_{1total}$ can be shown to be $$T_{1total}(\lambda, \rho_{ud}, \rho_{ld}, d_{ud}, d_{ld}) = \frac{T_{1ud}(\lambda, \rho_{ud}, d_{ud}) \times T_{1ld}(\lambda, \rho_{ld}, d_{ld})}{1 - R_{1ud}(\lambda, \rho_{ud}, d_{ud}) R_{1ld}(\lambda, \rho_{ld}, d_{ld})} \quad \text{Equation 5}$$

These equations can be extended, as is shown by W an et al. [1981], to an n layered system resulting in values for $R_{12\ldots n}$ and $T_{12\ldots n}$, of $$R_{12\ldots n} = R_{12\ldots(n-1)} + \frac{T_{12\ldots(n-1)}^2 R_n}{1 - R_{12\ldots(n-1)} R_n} \quad \text{Equation 6}$$

$$T_{12\ldots n} = \frac{T_{12\ldots(n-1)} T_n}{1 - R_{12\ldots(n-1)} R_n} \quad \text{Equation 7}$$

This system of equations can therefore compute the total remitted and transmitted light from an n layered system of arbitrary complexity provided that the thickness and composition of the layers is specified.

For the four-layer system shown in FIG. 2, this results in a value for the total light remitted and transmitted from the dermis dependent on $\lambda$, $\rho_{ud}$, $\rho_{ld}$, $d_{ud}$, $d_{ld}$, $d_{12}$, $\phi_{12}$, $d_{13}$ and $d_{13}$ where $d_{12}$ and $d_{13}$ are the thickness of layers 2 and 3 whilst $\phi_{12}$ and $\phi_{13}$ are their corresponding melanin densities. The thickness of layer 1 and layer 2 do not need to be explicitly defined as they are simply $d_{ud}-d_{12}$ and $d_{ld}-d_{13}$ respectively; similarly $\phi_{11}$ and $\phi_{14}$ are zero by definition. A further simplification is possible if it is assumed that $\phi_{12}=\phi_{13}$ leading to a single value of $\phi$ for the dermis.

The results of these equations can be combined with the predicted light transmitted by the epidermis in the same manner as that discussed in section 3.3 of the Technical Report, thus leading to the following description of total remitted, $S_{rd}$, and transmitted $S_{td}$.

$$S_{rd}(\lambda,\rho_{ud},\rho_{ld},d_{ud},d_{ld},d_{12},d_{13},\phi,d_m) = R_{2total}(\lambda,\rho_{ud},\rho_{ld},d_{ud},d_{ld},d_{12},d_{13},\phi)\theta(\lambda,d_m)^2 S(\lambda) \quad \text{Eqn. 8}$$

$$S_{td}(\lambda,\rho_{ud},\rho_{ld},d_{ud},d_{ld},d_{12},d_{13},\phi,d_m) = T_{2total}(\lambda,\rho_{ud},\rho_{ld},d_{ud},d_{ld},d_{12},d_{13},\phi)\theta(\lambda,d_m)^2 S(\lambda). \quad \text{Eqn. 9}$$

These can be used to predict the value of the corresponding LMS primaries $$L(\rho_{ud}, \rho_{ld}, d_{ud}, d_{ld}, d_{12}, d_{13}, \phi, d_m) = \qquad \text{Eqn 10}$$

$$\int_0^\infty R_{2total}(\rho_{ud}, \rho_{ld}, d_{ud}, d_{ld}, d_{12}, d_{13}, \phi)\theta(\lambda, d_m)^2 S(\lambda) S_L(\lambda) d\lambda$$

$$M(\rho_{ud}, \rho_{ld}, d_{ud}, d_{ld}, d_{12}, d_{13}, \phi, d_m) = \qquad \text{Eqn 11}$$

$$\int_0^\infty R_{2total}(\rho_{ud}, \rho_{ld}, d_{ud}, d_{ld}, d_{12}, d_{13}, \phi)\theta(\lambda, d_m)^2 S(\lambda) S_M(\lambda) d\lambda$$

$$S(\rho_{ud}, \rho_{ld}, d_{ud}, d_{ld}, d_{12}, d_{13}, \phi, d_m) = \qquad \text{Equation 12}$$

$$\int_0^\infty R_{2total}(\rho_{ud}, \rho_{ld}, d_{ud}, d_{ld}, d_{12}, d_{13}, \phi)$$

$$\theta(\lambda, d_m)^2 S(\lambda) S_S(\lambda) d\lambda$$

A further generalization can be made to any primary, $P_n$, leading to the following equation where $S_n$ defines the spectral response of that primary.

$$P_n(\rho_{ud}, \rho_{ld}, d_{ud}, d_{ld}, d_{12}, d_{13}, \phi, d_m) = \qquad \text{Equation 13}$$

$$\int_0^\infty R_{2total}(\rho_{ud}, \rho_{ld}, d_{ud}, d_{ld}, d_{12}, d_{13}, \phi)$$

$$\theta(\lambda, d_m)^2 S(\lambda) S_{P_n}(\lambda) d\lambda$$

This equation can then be used to generate the expected coloration of human skin exhibiting dermal descent of melanin.

The result of this analysis is that it is possible for the same coloration to result from different combinations of the above parameters. This complicates the measurement of the dermal invasion of melanin, (but not identifying the presence of any dermal melanin). Indeed, to obtain this measurement, it is necessary to know the amount of melanin in the overlying epidermis. However, at points where dermal invasion has taken place, this parameter is difficult to determine simply by comparing color co-ordinates of the abnormal location with color co-ordinates for healthy skin. It is for this reason that, in the present invention, regions where dermal melanin exists are identified by reference to a reference color co-ordinate range for healthy skin, and then the color co-ordinates of these regions are compared with the color co-ordinates at one or more normal skin locations. If said normal skin locations are adjacent to the region where dermal melanin exists, it is sufficient to use the epidermal melanin levels calculated for such normal skin locations to estimate the epidermal melanin levels at the region where dermal melanin exists. Alternatively, it is possible to perform a measurement of the epidermal melanin levels within areas of the skin where the presence of dermal melanin has been identified, by assessing the deviation in coloration at the blue end of the spectrum, from the reference color co-ordinate range for normal skin due to the presence of such dermal melanin. At the blue end of the spectrum, the increase in such deviation quickly slows with increasing depth of melanin penetration until a "saturation point" is reached. By assuming that the depth of melanin penetration within the dermis is large enough for such saturation to have occurred, an estimate of the deviation from the reference color co-ordinate range for normal skin can be made. This estimate allows a calculation to be made of the skin coloration assuming no dermal melanin, and therefore by reference to the color co-ordinate range for normal skin, of the level of epidermal melanin. It is within the scope of the present invention to measure the epidermal melanin levels directly, for example using polarized light, and to incorporate such measurements in the measuring step (ii) above.

By any of the above methods, the effect of what would have been the normal epidermal melanin level in the abnormal skin location can be taken into account, thereby enabling a more accurate determination of melanin descent.

By comparing the values of the skin image represented in a certain color space with theoretically calculated values covering all possible amounts of blood, dermal melanin penetration and melanin concentration within the same color space, the values of those three parameters can be obtained for every point in the image. Since the papillary dermis thickness and epidermal melanin content are known, it is possible to compute a detailed three-dimensional reconstruction of the top layers of human skin. This is of great potential interest to the medical profession and enables routine examination of the internal structure of living skin just as X-rays, NMR and ultrasound are used for examining other parts of the body. Other living tissue accessible by endoscope may also be examined, as may tissue which has been removed from a living or dead body. It is also within the scope of the invention to acquire the infra-red and/or visible images using lasers of different wavelengths or by using spectral analysis.

Deviations from the normal color surface may be due to unusual chromophores or constituents in the papillary dermis or epidermis: the nature and size of deviation gives information on the depth and concentration of these chromophores. Within pigmented skin lesions a particularly interesting chromophore is melanin, and its depth, concentration and distribution give useful information for the diagnosis of many skin conditions.

To assess such deviations it is important to understand that the deviation from the normal color surface is relative to the point on that surface relating to the amount of epidermal melanin. As such, knowledge of the amount of epidermal melanin allows examination in detail of the exact deviation which is due only to the chromophore in question. For instance, dermal melanin can vary in both its depth and concentration with a similar coloration or spectral properties being obtained from varying amounts of epidermal melanin and combinations of depth and concentration. This complicates the recovery of information relating to the depth and concentration of dermal melanin. If, however, the amount of epidermal melanin were known, an allowance could be made for it, or a measurement of the deviation could be obtained from the relevant position on the normal color surface where skin with such an amount of epidermal melanin would lie.

Such a measurement of epidermal melanin within regions of dermal melanin is complicated by the effect of the dermal melanin on the spectral remittance of the skin. However, a number of methods can be used to account for it:

1) Ascertain the amount of epidermal melanin in a region of skin adjacent the region with dermal melanin and interpolate this quantity into the melanistic region. This may be performed at a single location or at a number of points, e.g. surrounding the area of dermal melanin. Although such a measure is an interpolation it can give a good estimate allowing processing to proceed as described above.

2) If a technique is used as described with reference to Equation 32 below, a detector which is blind to epidermal melanin can be used to investigate such regions. This utilizes a technique where epidermal melanin is assessed using a set of detectors and algorithms which have a zero or constant response to varying amounts of epidermal melanin. Variations in dermal melanin, or other chromophores, however will still elicit a response allowing the construction of look-up tables relating the output of such sensors to variations in these constituents. Such a technique would not suffer from the effects of overlying epidermal melanin as it is blind to it.

3) To obtain highly accurate measures of dermal melanin penetration and concentration, it is preferable to ascertain the amount of epidermal melanin, however, it is possible to obtain useful information without such a correction. By varying the amount of dermal melanin and concentration either mathematically or by biological studies it is possible to measure the maximum possible deviation from the surface of normal skin coloration. In general as the 'corrected for collagen variations' skin coloration or spectral properties nears this maximum the deeper the dermal melanin lies in the papillary dermis. Therefore by ascertaining the ratio of distance from the surface of normal skin coloration to such a measure relative to its distance from the maximal values a measure of depth can be made.

It is possible to use a computer programmed with the above algorithms to perform the actual calculations. However, before these calculations can be performed, an image of the area of skin under investigation must be represented in the same color space as for the normal skin reference color co-ordinate range. This can be done in a number of ways. In one way, the skin color co-ordinates are acquired from an image using the same lighting conditions and a CCD camera calibrated in the same way as that used to produce the healthy skin reference color co-ordinate range. Alternatively, if exactly the same lighting conditions are not used, a white standard or other appropriate correction factor can be used to allow calibration of the image within the software. As a further alternative, a color image can be acquired using a color photographic film which is then digitized. This can be performed using either exactly the same lighting conditions and a calibrated set-up or again with the inclusion of a white standard or other appropriate correction factor. It is within the scope of this invention to obtain both the infra-red and visible images with a single digital camera or to calculate the value of the necessary primaries through the use of spectroscopy.

A method and apparatus according to the invention are valuable in providing information to a clinician on which the clinician may base a diagnosis or a course of treatment and the apparatus may be used for controlling the treatment and in some cases for giving an indication of whether the treatment may be effective or not. Some preferred embodiments of the invention are applied for controlling a treatment which involves the irradiation of a region of tissue with treatment light of predetermined spectral characteristics, wherein the absorption characteristics of tissue supervening the region to be treated for the treatment light are measured and used in calculating a required exposure of the tissue to the treatment light, or for predicting the outcome of a treatment which involves the irradiation of a region of tissue with treatment light of predetermined spectral characteristics, wherein the absorption characteristics for the treatment light of the tissue region to be treated and of tissue supervening the region to be treated are measured and used in calculating a required therapeutically effective exposure of the tissue to the treatment light, and the required exposure and the absorption characteristics of the supervening tissue are used to predict potential destruction or scarring of the supervening tissue by such exposure.

For example, haemangioma (so-called port-wine stains, due to an abnormal distribution of blood vessels) may be diagnosed by straight-forward visual inspection, and it is well known to treat the condition by laser to cauterize the blood vessels. Typically treatment for such a problem begins with the firing of a series of "test shots" by a laser at different powers to establish the minimum power necessary to cauterize the blood vessels. That power will depend on the depth and the size of those vessels, and these may vary over the extent of the lesion. The test powers are chosen by the clinician having regard to his skill and past experience. This technique suffers from a number of disadvantages. It is not very reliable since the depth and the size of the blood vessels may vary over the extent of the lesion. It is time consuming since the results of the test need to be assessed after a healing time. And the patient is left in a state of uncertainty during that time. This uncertainty is exacerbated due to the fact that a too intense laser irradiation will result in burning of the skin and consequent permanent scarring. In the cases of up to about one third of patients, the intensity of irradiation which would be required to cauterize the offending blood vessels is actually so high that there would be a serious risk of scarring and the treatment is accordingly contra-indicated.

The present invention can be used to establish not only the amount of blood present, and thus give an indication of the amount of blood vessels required to be cauterized, but also the depth of those vessels beneath the surface of the skin. In addition the invention can be carried out in such a way as to calculate the amount of melanin and any other unwanted energy-absorbing chromophores, such that through a knowledge of the spectral absorption characteristics of these chromophores and the spectral characteristics of the incident treatment light an estimate can be made of the energy absorption of these chromophores and therefore the amount of unwanted heating of the supervening or other tissue that would be unavoidably irradiated during treatment. The intensity of laser irradiation needed to cauterize a given amount of blood vessels is known from past experience or can be established, and the absorption characteristics of human skin in relation to the laser radiation of a given wavelength can readily be established (indeed handbooks supplied with medical lasers tend to contain this information).

Thus by making use of the present invention, light remitted from the stain can be analyzed to give an indication of the melanin content of the epidermis (which governs its absorption coefficient) and of the depth and concentration of the offending blood vessels, and a prediction can be made there and then as to the intensity of laser irradiation which will be required to effect a satisfactory treatment and whether that intensity would give an acceptably low risk of permanent scarring. Further this assessment may be made at as many points over the extent of the stain as are thought necessary. Not only that, but the output signal from the apparatus may be used to control firing of a laser. Thus the power output of the laser may be varied as it is directed over the extent of the lesion. Thus the laser may be controlled to give the minimum effective power dissipation over the various increments of the lesion. Parts only of the area of the lesion could be treated if that would give a cosmetically acceptable result. And if the lesion was so severe that it was unsuitable for laser treatment, the patient could be told immediately and would not face some weeks of uncertainty.

The present invention can thus also be used to predict the outcome of a given course of treatment. This may be achieved by predicting the effect of treatment on the quantity of the chromophore to be eliminated or stimulated. This can be done by correlating experimentally the energy reaching the chromophore with the effect produced by that energy, and by measuring the structure and chromophore before and following treatment. Using this predictive data, the predicted change in a tissue sample can be calculated by measuring that sample and calculating the energy reaching that chromophore, relating that energy to a predicted change in that chromophore through the experimental correlation, and then recalculating the effect of that revised chromophore level on the tissue appearance using the optical model described in this document.

Similar considerations apply in the case of removing tattoos by the destruction of the pigments used to make them, and in the destruction of melanin/melanocytes during the removal of moles. Similar considerations also apply in the case of the stimulation of collagen growth using light energy to stimulate collagen-producing cells.

The removal of hair by laser cauterization of the hair bulb may also be controlled by apparatus according to the invention. Hair consists of keratin and its color (and thus light energy absorption characteristics) is due to the presence of melanin. The hair bulb is located in or below the reticular dermis. Using the present invention it is possible to determine the absorption characteristics of the skin layers which would have to be penetrated by laser radiation aimed to destroy the hair bulb. The absorption characteristics of the hair bulb can be measured or calculated from a measurement of the melanin content of the hair, and the amount of energy which would have to be absorbed by the hair bulb to destroy it can also be determined, in vitro if necessary. From this information, it is possible to calculate the energy which would require to be dissipated by the laser, and it would accordingly be possible either to give a minimum energy dosage, or to predict that the minimum required dosage was so high that permanent scarring would result and that the treatment should accordingly not be carried out.

It will be appreciated that the output signal generated by the use of the invention will represent an average value over the extent of the area monitored: this will plainly be no greater than the size of the light spot which is illuminated, and its size may also be determined by the size of the photoreceptor. Means may be provided for varying the monitored area if desired, for example from a spot 0.1 mm or less (e.g. 0.01 mm) to 10 cm or more in diameter. This can be extended to provide an image of an area by providing the analysis at a number of locations. This can easily be achieved by the use of a digital camera.

To achieve these results, the system measures the light remitted from skin and compares it with the incident light at a number of wavelengths or wavelength bands. These measurements can be performed using any convenient means including filters or a spectrometer and they allow quantification of the quantities and position, including distance relative to the dermo-epidermal junction, of chromophores such as collagen, melanin, blood and keratin. Indeed these measurements can be performed on any substance assuming its absorbency and reflectivity of light are known. "Spectral measurement" is used to denote measurement of the light remitted from human skin whether by the use of a spectrometer or sub-sampling through filters which can be placed in the path of the incident or remitted light. The spectral measurements can be performed at one or more points. A collection of points whether gathered simultaneously or not can also be combined to form an image showing the measurements over the skin.

The spectral remittance of light from human skin can be calculated given knowledge of the quantity and position of substances within it. Such calculations can be performed using a variety of mathematical means including Monte Carlo modeling and the Kubelka-Munk theory, generating a value for $P_n$ where $$P_n(\rho_1, \rho_2, \rho_3 \ldots \rho_n, d_1, d_2, d_3 \ldots d_n, \phi_{m1}, \phi_{m2}, \phi_{m3} \ldots \phi_{mn}, d_m, v, \kappa) = \frac{\int_0^\infty R(\rho_1, \rho_2, \rho_3 \ldots \rho_n, d_1, d_2, d_3 \ldots d_n, \phi_{m1}, \phi_{m2}, \phi_{m3} \ldots \phi_{mn}, v)\theta(\lambda, d_m, \kappa)^2 S(\lambda) S_{P_n}(\lambda) d\lambda}{\int_0^\infty S(\lambda) S_{P_n}(\lambda) d\lambda}$$

Equation 14 in which:

$P_n$ represents the calculated or measured ratio of remitted to incident light for a particular wavelength function or filter $S_{P_n}(\lambda)$ and incident light $S(\lambda)$. $\theta$ represents the light absorbed within the epidermis with dm representing the quantity of epidermal melanin and $\kappa$ the amount of keratin. R represents the ratio of light remitted from the dermis to light incident on the dermis, with $\rho_1, \rho_2, \rho_3 \ldots \rho_n$ representing the quantity of blood within n layers within the dermis, parallel with the skin surface and of thicknesses $d_1, d_2, d_3 \ldots d_n$. Within these layers, $\phi_{m1}, \phi_{m2}, \phi_{m3} \ldots \phi_{mn}$ represent the quantity of melanin within the dermis and $v$ the thickness of the papillary dermis. $P_n$ can also be obtained through measurements on real skin rather than by calculation.

As discussed the position within the dermis and concentration of blood is of importance to the calibration and use of medical lasers. The position of such blood will effect the remitted light from the skin generally causing the skin color to become more purple as the depth of blood vessels increases.

To ascertain non invasive information regarding blood position and concentration the spectral composition of light remitted from skin can be ascertained as above for a representative sample of possible blood quantities and blood depths. It is also necessary to generate the possible set of remitted light measurements relating to variations in other parameters such as epidermal melanin, dermal melanin, papillary dermal thickness and keratin. As such an N dimensional search space is generated where N corresponds to the number of different constituents and blood and melanin planes considered. This analysis can be extended to include any other constituents such as tattoo pigment. For analysis of skin this may have to include spectral measurements within the infrared portion of the electromagnetic spectrum as well as the visible.

Measurements of the spectral remittance from skin to be examined are then compared with the data within the N dimensional search space with the closest match indicating the constituents of the skin. The data for these comparisons can either be performed as required or incorporated into pre calculated lookup tables.

Such an analysis may require a large search and it is possible for certain combinations of constituents to generate the same spectral remittance and thus multiple solutions.

Another approach is to identify those constituents of skin about which information can reliably be ascertained, quantify these and perform a transformation to the measured spectral remittance or data to which this is to be compared.

This can for instance be achieved by first adjusting for variations in the thickness of the papillary dermis in the manner described above. A second quantity that must also be assessed is the quantity of melanin within the epidermis. The accuracy to which this can be assessed has a large influence on the accuracy to which the depth of blood within the dermis can be ascertained. However the presence of blood at different depths within the dermis markedly changes the remittance of light from the skin and so complicates the assessment of epidermal melanin levels by standard spectroscopic means.

A solution to this problem assumes that the quantity of epidermal melanin does not change markedly over the skin surrounding the lesion thus allowing interpolation from the surrounding areas. Such a technique may operate in certain lesions but the reliance that can be placed on the results will be lowered. A second solution is to assess the levels of epidermal melanin by a spectroscopic/light analysis method accepting any inaccuracies due to the complicating factor of blood at different depths. Following either of these techniques the N dimensional space can be reduced requiring only solutions to $P_{nr}$ to be found where $$P_{nr}(\rho_1, \rho_2, \rho_3, d_1, d_2, d_3) = \int_0^\infty R_{nr}(\rho_1, \rho_2, \rho_3, d_1, d_2, d_3) S(\lambda) S_{P_n}(\lambda) d\lambda \quad \text{Equation 15}$$

As discussed inaccuracies in this measurement will adversely effect the assessment of blood position within the dermis thus lowering its accuracy.

A third solution is to use a detector which is "blind" to the effect of melanin within the epidermis. Such a detector would register zero, or a constant value, when presented with melanin within the epidermis with differences in its value corresponding purely to the quantity and position of other skin constituents. Such a detector would not require transformations to data based on measures for the amount of epidermal melanin thus increasing accuracy. It is also possible to use such a detector in the generation of the N dimensional search space discussed previously.

The epidermal-melanin-blind detector renders the pigment melanin effectively transparent when it lies within the epidermis of the skin. Such a detector allows viewing of structures within the skin with the obscuring effect of epidermal melanin removed. The approach outlined utilizes knowledge of the variation of light absorption by melanin within the epidermis with wavelength. The use of polarized light affords advantages in achieving melanin-blind results.

At a particular wavelength $\lambda$, let the ratio of remitted to incident light from skin be $P(\lambda)$. If two wavelengths $\lambda_1$ and $\lambda_2$ are considered this leads to two values of P, $P(\lambda_1)$ and $P(\lambda_2)$.

Let $R_d(\lambda,\upsilon)$ represent the ratio of remitted to incident light from bloodless, melanin-free, normal dermis with a known quantity of collagen within the papillary dermis $\upsilon$. Further let $\theta(\lambda,d_m)$ represent the ratio of incident to transmitted light for melanin where $d_m$ represents the quantity of melanin. It can be shown that $P(\lambda)=\theta(\lambda,d_m)^2 R_d(\lambda,\upsilon)$, and therefore $$P(\lambda_1)=\theta(\lambda_1,d_m)^2 R_d(\lambda_1,\upsilon) \quad \text{Equation 16}$$

and $$P(\lambda_2)=\theta(\lambda_2,d_m)^2 R_d(\lambda_2,\upsilon). \quad \text{Equation 17}$$

As further shown in "*The optics of human skin*" The Journal of Investigative Dermatology, (R. Anderson, B. Parrish & J. Parrish), $\theta(\lambda,d_m)$ can represented in the form $$\theta(\lambda,d_m)=e^{-d_m m(\lambda)} \quad \text{Equation 18}$$

where $m(\lambda)$ is the spectral absorption coefficient of melanin. As such Equations 16 and 17 become $$P(\lambda_1)=e^{-2d_m m(\lambda_1)} R_d(\lambda_1,\upsilon) \quad \text{Equation 19}$$

and $$P(\lambda_2)=e^{-2d_m m(\lambda_2)} R_d(\lambda_2,\upsilon) \quad \text{Equation 20}$$

By taking the natural logarithm of both sides of the equations, equations 19 and 20 can be shown to equate to $$\ln P(\lambda_1)=\ln e^{-2d_m m(\lambda_1)}+\ln R_d(\lambda_1,\upsilon) \quad \text{Equation 21}$$

and $$\ln P(\lambda_2)=\ln e^{-2d_m m(\lambda_2)}+\ln R_d(\lambda_2,\upsilon) \quad \text{Equation 22}$$

which can be simplified to $$-2d_m m(\lambda_1)=\ln P(\lambda_1)-\ln R_d(\lambda_1,\upsilon)=V_1 \quad \text{Equation 23}$$

and $$-2d_m m(\lambda_2)=\ln P(\lambda_2)-\ln R_d(\lambda_2,\upsilon)=V_2 \quad \text{Equation 24}$$

The proposition for an epidermal blind detector is that $V_1-CV_2=0$ where C is a constant. For this to be true:

$$-2d_m m(\lambda_1)+2C d_m m(\lambda_2)=0 \quad \text{Equation 25}$$

and therefore $$C = \frac{m(\lambda_1)}{m(\lambda_2)} \quad \text{Equation 26}$$

leading to $$\ln P(\lambda_1)-\ln R_d(\lambda_1,\upsilon)-C(\ln P(\lambda_2)-\ln R_d(\lambda_2,\upsilon))=0 \quad \text{Equation 27}$$

This discussion assumes bloodless skin where the only melanin present exists in the epidermis. For real skin however this will often not be the case, with blood, melanin in the dermis and keratin etc. being present. In this situation an extra term $E(\lambda)$ is introduced to the right hand side of Equations 21 and 22 representing the extra absorption, or indeed reflectance, introduced through the additional constituents leading to $$\ln P(\lambda_1)=\ln e^{-2d_m m(\lambda_1)}+\ln R_d(\lambda_1,\upsilon)+\ln E(\lambda_1) \quad \text{Equation 28}$$

and $$\ln P(\lambda_2)=\ln e^{-2d_m m(\lambda_2)}+\ln R_d(\lambda_2,\upsilon)+\ln E(\lambda_2) \quad \text{Equation 29}$$

and therefore $$\ln P(\lambda_1)-\ln R_d(\lambda_1,\upsilon)-C(\ln P(\lambda_2)-\ln R_d(\lambda_2,\upsilon))=\ln E(\lambda_1)-C \ln E(\lambda_2)=F \quad \text{Eqn 30}$$

As $P(\lambda_1)$ and $P(\lambda_2)$ can be measured, C is known, and $R_d(\lambda_1,\upsilon)$ and $R_d(\lambda_2,\upsilon)$ can be calculated as disclosed in the International Patent Application published as WO 98/22023, F can thus be calculated. The value of F therefore indicates information about the extra terms $E(\lambda_1)$ and $E(\lambda_2)$ with $$F=C \ln E(\lambda_2)-\ln E(\lambda_1) \quad \text{Equation 31}$$

and therefore $$e^F = \frac{E(\lambda_2)^C}{E(\lambda_1)}$$ Equation 32

In summary, to operate the epidermal melanin blind detector measurements $P_1$ and $P_2$, where $P_1=P(\lambda_1)$ and $P_2=P(\lambda_2)$, of skin are made and $R_1$ and $R_2$, where $R_1=R_d(\lambda_1,\upsilon)$ and $R_2=R_d(\lambda_2,\upsilon)$, are calculated. F is then calculated from ln $P_1$−ln $R_1$−C(ln $P_2$−ln $R_2$) with its value giving information about pigments and components other than epidermal melanin.

The above analysis is based on the use of two measurements at two separate frequencies. However this can be extended to broad band filters with values of m, the spectral absorption coefficient of melanin, calculated for each broad band filter.

As $E(\lambda)$ relates purely to the change in remitted light, whether absorbed or reflected, without reference to the quantity of epidermal melanin or papillary dermal thickness it is simple to calculate it for blood at different quantities and depths within the dermis. The measured values of $E(\lambda)$ can then be compared with these thus returning information regarding the depth of blood vessels.

This approach can be extended to analyze constituents other than blood with the removal of epidermal melanin such as the examination of keratin, tattoo pigments, dermal melanin etc. Indeed the concept of a melanin blind detector can be extended to a blood blind detector, tattoo pigment blind detector and indeed any constituent for which the light reflectance and absorbency are known.

By allowing an accurate measurement of the depth and concentration of blood vessels and other constituents, these measurements can then be used within Equation 14 thus allowing an accurate measurement of epidermal melanin.

The knowledge gained regarding the position and constituents of human skin can be utilized in Equation 14 to form a number of important measures. For instance the percentage of light at any particular wavelength, or wavelength band, which is absorbed by epidermal melanin can be ascertained. This information can then be used to calculate the likelihood of scarring occurring and thus allow the setting of a safe maximum intensity of light, whether through a laser or other illumination device, that can be applied to the skin.

Further, the intensity, or percentage of light, passing through the entire papillary dermis can be ascertained. This is calculable using an equation similar to Equation 14 to result in the ratio, T, of incident light to light passing through the entire papillary dermis being calculated for a particular wavelength function or filter $SP_n(\lambda)$ and incident light $S(\lambda)$.

$$T(\rho_1, \rho_2, \rho_3 \ldots \rho_n, d_1, d_2, d_3 \ldots d_n, \phi_{m1}, \phi_{m2}, \phi_{m3} \ldots \phi_{mn}, d_m, v, \kappa) = \frac{\int_0^\infty T_d(\rho_1, \rho_2, \rho_3 \ldots \rho_n, d_1, d_2, d_3 \ldots d_n, \phi_{m1}, \phi_{m2}, \phi_{m3} \ldots \phi_{mn}, v)\theta(\lambda, d_m, \kappa)^2 S(\lambda) S_{P_n}(\lambda) d\lambda}{\int_0^\infty S(\lambda) S_{P_n}(\lambda) d\lambda}$$ Equation 33

$T_d$ represents the light transmitted through the papillary dermis and can be calculated using a variety of mathematical means including Monte Carlo modeling and the Kubelka-Munk theory.

Such a measure is useful in quantifying the intensity that might impinge on a hair bulb and thus can be used to judge the efficacy of hair removal by laser or other light source.

Similarly the intensity or percentage of light that reaches blood at a particular depth can be ascertained and from this the quantity absorbed by the blood. Such a measure allows an assessment or calculation of the effectiveness of the light in treating the blood vessels.

Following the quantification of the intensity of light impinging on various structures it is possible to ascertain, or quantify, the effect such an intensity will have on these structures. This may be performed through calculation or through analysis of previous treatments or through laboratory experiments. This knowledge then allows calculation, through Equation 14, of the expected appearance of the skin at either a particular wavelength or wavelength band following the application of such light. This information could, for instance, be used to generate color, RGB, representations of the expected result of a treatment which would be of great use in the planning of such treatment.

In preferred embodiments of the invention, the spectral analysis is undertaken at more than one, for example at least four, distinct wavelengths or wavelength bands, and in some preferred embodiments, such analysis is undertaken over the whole spectrum. In a simple construction of apparatus, a filter wheel is placed between the source of illumination, and the area of skin under inspection is successively illuminated using light of the desired different wavelengths or wavelength bands. In that case, all that is necessary is to measure the intensity of remitted light for each wavelength (band). Alternatively, white light may be used and the remitted light measured by a spectrometer to give values at each of a plurality of narrow wavelength bands covering substantially the entire spectrum.

The use of narrow wavelength bands, whether due to filtering incident or remitted light or by use of a spectrometer, has advantages in certain circumstances. For example, it may be desired to distinguish between arterial blood and venous blood. Arterial and venous blood have slightly different spectral characteristics due to the presence or absence of oxy-haemoglobin. Both oxy-haemoglobin and haemoglobin remit light strongly in the red, and their spectral curves in fact largely overlap. However, venous blood, without oxy-haemoglobin has a spectral curve with a domed peak, whereas arterial blood, due to the presence of oxy-haemoglobin has a spectral curve with twin peaks separated by a valley. The use of two narrow band filters, one at a wavelength corresponding to one or other of those peaks, and one at a wavelength corresponding to the valley in the oxy-haemoglobin spectrum and a comparison of the intensity of light remitted at those wavelengths can thus determine the presence or absence of oxy-haemoglobin and thus distinguish between venous and arterial blood.

The analysis of at least four different wavebands offers considerable advantages over previous proposals, and allows the system to be used for measuring a variety of different parameters which could not previously have been unambiguously derived from the information given. For example, it allows the offset of chromophores to be measured. By offset, we mean the distance between the dermo-epidermal boundary and the top of the population of chromophores. This is in addition to the concentration and depth of the chromophores. The problem was that the position of a spot within a three-dimensional CIE LMS color space was not necessarily unique to a given set of measurements. The same position could be achieved by relative variation between two of the variables concerned. Previously, it had been necessary to make an estimate based on prior assumptions about the relationship between these variables. The analysis of a fourth or further wavelength band allows comparison with a notional color space having four (or more) dimensions so that any position within that N dimensional space can be attributed to a unique depth, concentration and offset of a particular chromophore.

The present invention at least in its most preferred embodiments, enables the generation of information regarding a number of features regarding skin. To allow an accurate diagnosis of disorders of the skin, or the prognosis of treatment for such disorders, or the monitoring of healthy skin, it is important that the spatial relationship between these features can be understood. To facilitate the spatial correlation of two images, one showing the appearance of the skin and the other showing a particular feature or of two images showing different features, we have developed a technique whereby a third image is generated. Thus we also provide a method of and apparatus for showing both images together with the proportion or intensity of each adjusted through the use of a control of some means and this allows spatial correlation of the input images. For example the two original images might be supplied in overlapping relation to a monitor screen of a PC, and the two images be relatively faded in and faded out in order to change from viewing one image to another.

The display first shows an image, which may or may not be magnified, of the lesion as it actually appears to the eye or a surface microscopy view or an image taken using cross polarized illumination or an image showing a particular feature. By selecting a particular feature such as blood or areas of melanin invasion into the dermis or melanin within the epidermis etc. the display can then be faded to show this feature as an image. The fading allows a progression, or mixing, between the two views and is a convenient means of allowing a spatial correlation to be made between the features and the lesion image.

The images may be images representing the presence of particular existing features of the skin or one or more of them may be computer generated images representing the predicted effects of a treatment such as a laser irradiation treatment. For example, as mentioned above, it is possible to generate a color representation of the expected result of a laser irradiation treatment, and it would be possible to generate one such image for each of a set of different irradiation intensities. This would enable a comparison of the different courses of treatment and would allow selection of an appropriate treatment, for example the one giving the most cosmetically acceptable result.

The analysis afforded by the present invention is also of value in the selection of the wavelength or wavelengths of any light (infra-red, visible or ultra-violet) irradiation treatment that may be indicated. For example, a knowledge of the constituents of a lesion allows a selection of a wavelength of light radiation which will be most strongly and preferentially absorbed by constituents of that lesion. Also, a knowledge of the existence and structure and composition of overlying tissue (including any discontinuities which it might contain) allows the most favorable compromise to be reached between low absorption in the overlying tissue and high absorption in the lesion to be destroyed, thus providing the most effective treatment with the lowest radiation dosage. Thus a laser of an appropriate wavelength may be selected, and/or a variable wavelength laser may be tuned, or an appropriate filter set may be used in conjunction with a source of non-coherent radiation.

Such a technique may be applied not only to the skin as described above, but also to other epithelial or layered tissue of the human or animal body. Such tissues include the epithelium of the cervix, the lining of the mouth, epithelia of the respiratory and digestive tracts and the eye, including such specialized tissues as the sclera, cornea and retina, and epithelia of internal organs such as the liver and bladder.

The mathematical model described accounts for components such as blood, melanin and collagen, and is generally applicable to epithelial or layered tissues. It is therefore possible to predict the coloration or spectral composition of the tissue containing different amounts of these components. Characteristics of the components can thus be determined by an examination of measured spectral properties in the manner described.

For example, the cervix is covered with a stratified squamous epithelium in which the distribution of blood, collagen and melanin may be determined, and information relating to this is useful in the monitoring and diagnosis of the general state of health especially with regard to cervical cancer. A second example relates to the interior of the human eye. This includes various specialized tissues such as the sclera, cornea and retina containing blood, collagen and melanin in a layered structure. Information on the distribution of these components is useful in monitoring the health of the eye.

In each case, the technique and mathematical model described can be adapted to take account of particular or additional light absorbing or light scattering components or present in the tissue examined.

According to one particular aspect of the invention, a method of mapping the papillary surface of an area of the dermis is provided.

The invention thus provides a way of obtaining a map which indicates the contours of the papillary surface of the dermis. In its simplest form, this map is simply a line such as may be seen on a suitably prepared section of biopsied skin. However, such line may be derived without incision and accompanying risk of infection, and it may also be derived and inspected very much more quickly and without discomfort to the patient.

This and other aspects of the invention are based on a realization that the thickness of the papillary dermis may be obtained by utilizing the property of human skin to vary its remittance of red and infrared radiation with varying papillary dermis thickness. In general, there is a relationship between remittance and thickness. The fact that red or infrared radiation is also absorbed by other materials within the skin, particularly melanin and blood, is a complicating factor, but the layer thickness may still be measured by obtaining two red or infrared images, each at a different wavelength. The chosen wavelengths are not important, but one should be further into the infrared (i.e. at longer wavelength) than the other. Suitable wavelength bands are, as before, 800-1000 nm and 600-800 nm, in that readily available infrared films and filters may be used. The brightness of points within the image obtained at the longer wavelength is affected to a greater extent by variations in the papillary dermis thickness. Conversely, the image obtained at shorter wavelength will be affected to a greater extent by other materials such as melanin and blood. (In fact when operating sufficiently far into the infrared, say at 1100 nm, the effects of melanin and blood become negligible, and it is possible to derive the necessary information using a single wavelength measurement. But this greatly increases the cost of the detection and monitoring equipment.) By predicting the brightnesses of points of differing papillary dermis thickness and amounts of epidermal melanin which absorb near-infrared radiation at the two different infrared wavelengths, a reference graph (FIG. 1) can be obtained which consists of lines of constant papillary dermis thickness, wherein Primary 1 is the measurement made at the longer (800-1000 nm) wavelength and Primary 2 is the measurement made at the shorter (600-800 nm) wavelength. The absorption of blood within these wavelengths is very small (a hundredth of its peak value for visible wavelengths at 600-800 nm and even less for 800-1000 nm) and to a first approximation may be ignored. Thus, by comparing values obtained at these wavelengths with this graph, it is possible to ascertain the papillary dermis thickness. However it is within the scope of the present invention to measure brightness at such a long infra-red wavelength e.g. 1100 nm that the brightness would vary to such a negligible extent with melanin and blood content that it would effectively depend solely on the papillary dermis thickness. In such a case only one set of brightness measurements would be required.

To calculate the look-up graph shown in FIG. 1 the spectral remittance of light from human skin can be calculated given knowledge of the quantity and position of substances within it. Such calculations can be performed using a variety of mathematical means including Monte Carlo modeling and the Kubelka-Munk theory generating a value for $P_n$ where $$P_n(\rho, d_m, v) = \frac{\int_0^\infty R(\rho, v)\theta(\lambda, d_m)^2 S(\lambda) S_{P_n}(\lambda) d\lambda}{\int_0^\infty S(\lambda) S_{P_n}(\lambda) d\lambda} \quad \text{Equation 34}$$

where $P_n$ represents the calculated or measured ratio of remitted to incident light for a particular wavelength function or filter $S_{P_n}(\lambda)$ and incident light $S(\lambda)$. $\theta$ represents the light absorbed within the epidermis with $d_m$ representing the quantity of epidermal melanin. R represents the light remitted from the dermis with $\rho$ representing the quantity of blood and $v$ the thickness of the papillary dermis. $P_n$ can also be obtained through measurements on real skin rather than by calculation.

This analysis can be extended to a more general case $$P_n(\rho_1, \rho_2, \rho_3, \ldots, \rho_n, d_1, d_2, d_3, \ldots, d_n, \phi_{m1}, \phi_{m2}, \phi_{m3}, \ldots, \phi_{mn}, d_m, v, \kappa) = \frac{\int_0^\infty R(\rho_1, \rho_2, \rho_3, \ldots, \rho_n, d_1, d_2, d_3, \ldots, d_n, \phi_{m1}, \phi_{m2}, \phi_{m3}, \ldots, \phi_{mn}, d_m, v)\theta(\lambda, d_m, \kappa)^2 S(\lambda) S_{P_n}(\lambda) d\lambda}{\int_0^\infty S(\lambda) S_{P_n}(\lambda) d\lambda} \quad \text{Equation 35}$$

Where $\kappa$ represent the amount of keratin and $\rho_1, \rho_2, \rho_3, \ldots, \rho_n$, the quantity of blood within n planes within the dermis parallel with the skin surface of thickness $d_1, d_2, d_3, \ldots, d_n$. Within these planes, $\phi_{m1}, \phi_{m2}, \phi_{m3}, \ldots, \phi_{mn}$, represent the quantity of melanin within the dermis. As with the simple case $P_n$ can also be obtained through measurements on real skin rather than by calculation. For a detailed discussion of this technique please refer to "*A non-invasive imaging system for assisting in the diagnosis of melanoma*" University of Birmingham, Symon Cotton, 1998.

The above discussion relates to measurements of the thickness of the papillary dermis alone. However, according to *Histology, a text and atlas*, second edition, Michael Ross and Lynn Romrell, published by Williams & Wilkins, "The papillary layer consists of loose connective tissue. It is located immediately under the epidermis and is separated from it by the basal lamina. The papillary layer is a relatively thin layer extending into (and, thus, also constituting) the dermal papillae and ridges." In contrast the junction between the papillary dermis and reticular dermis is relatively smooth or at least varying with a wavelength very large in contrast to the undulations of the papillary dermis.

It is apparent from this as the thickness of the papillary dermis, $v$, refers to a particular sampling point, or rather the average over a sampling area, measurements taken at a variety of points return information on the thickness of the papillary dermis at these points. Further to this if it is assumed that the papillary dermis constitutes the dermal papillae and also that the junction between the papillary dermis and reticular dermis is smooth, or at least varies on a scale much larger than the dermal papillae, measurements made from a series of points $v_1, v_2, v_3, \ldots, v_n$, as shown in FIG. 8, will—if displayed spatially—show the undulations in the papillary dermis. Further measurements can be performed on the height of a particular dermal papilla by subtracting a local minimum, shown in FIG. 8 as min1 ($v_2$), from a local maximum, shown in FIG. 8 as max1 ($v_1$). Examples showing dermal papillae generated using this method are shown in FIGS. 12 and 13.

As discussed further by Ross and Romrell "They [dermal papillae] are complemented by what appear to be a series of similar projections or evaginations, called epidermal ridges or rete ridges, which project into the dermis." It is clear from this that information regarding the rete ridges can be obtained in a similar manner as the rete ridges and dermal papillae fit together and are therefore the inverse of one another. For instance the depth of an individual peg being calculated from max1−min1. To generate a three dimensional representation or two dimensional segment showing a number of rete ridges requires a calculation, $C-v_n$, where C is a constant greater than any of the max1−max2 measurements.

It is apparent from this that measurements of the papillary dermis thickness, $v$, measured over an area or along a line when suitably interpreted can impart information regarding the dermal papillae and rete ridges. In particular if the thickness of the papillary dermis is measured over an area or along a line and then shown graphically the undulations of the dermal papillae can be observed. As the rete ridges extend down from the epidermis filling the void between the dermal papillae it also becomes evident that the inverse of such a measure—such as a constant value minus the papillary dermis thickness—gives information regarding the rete ridges.

An example of this is shown in FIG. 9 where the dermal papillae pertaining to an area of skin in the shoulder region are shown rising from the dermis. In conjunction with this the rete ridges can be seen descending.

In the most preferred embodiments of the invention, means is provided for monitoring the intensity of the light remitted from a plurality of lines or a two-dimensional array of points, and preferably with a resolution of at least 20 lines or dots per mm.

This allows the production of an analogue of a three-dimensional image which can be printed or displayed on a monitor screen, and in the latter case, the use of suitable software will enable the image to be rotated so that its appearance can be viewed from a plurality of different angles.

A higher resolution may be obtained, and will indeed be necessary if inspection of a highly magnified image of the remitted light is to be obtained, but our tests have shown that a very high resolution is not necessary for many purposes. In a particularly preferred apparatus, an image of remitted light is captured using a digital camera in which use is made of a charge coupled device measuring 20×15 mm with a resolution of 800×600 pixels.

Such an image may take the form of a series of lines each of which follows the contour of the mapped surface while remaining constant in one of three orthogonal axes. Alternatively, it may comprise lines of equal contour, or it may be constituted as a continuous tone or colored picture of the papillary surface over the area being inspected.

It is implicit in what has been stated above that no account is taken of any variations in the shape of the boundary between the papillary dermis and the reticular dermis at the intradermal junction. It is assumed that the intradermal junction is flat. In fact, as mentioned there are variations in the thickness of the papillary dermis when the presence of those papillae is discounted, but those variations are of long wavelength in comparison with variations due to the papillae and they may be neglected.

Inspection and analysis of the architecture of the dermal papillae and the epidermal rete ridges at the dermo-epidermal junction allows information to be derived which is of considerable importance to clinicians in order to assist them in diagnosing or assessing the progress of a range of dermatological phenomena.

Examples include the blistering diseases *Pemphigus vulgaris* and bullous pemphigoid. While these diseases appear clinically similar, they have very different prognoses and they require different management. *Pemphigus vulgaris* manifests itself as blisters within the thickness of the epidermis which do not distend the local dermo-epidermal boundary architecture, and it is potentially fatal with a 10% mortality rate. Bullous pemphigoid, however, gives rise to sub-epidermal blistering which does distend the local dermo-epidermal boundary architecture: prognosis is good, and the disease tends to subside over a number of months.

The dermo-epidermal boundary architecture is important in the differentiation between benign and malignant melanoma, and in identifying the presence of fibrosis within a melanoma. It is also important when assessing the extent of basal cell carcinomas and squamous cell carcinomas.

The present invention includes any method of analyzing biological tissue comprising illuminating the tissue with light, spectrally measuring and analyzing the differences between the incident and remitted light, the analysis of this data to define a parameter of the tissue, the normalization of the data to a standard value of that parameter using a predictive mathematical model of the optical properties of the biological tissue, and the subsequent measurement of a further parameter from that normalized data, preferably with more than one sequential normalization and analysis step to define further parameters.

The invention also extends to any method for analyzing biological tissue comprising the illumination of the tissue with light, the spectral measurement of the differences between the incident and remitted light, the analysis of these data by comparison of features present within these data with a previous mapping of these features to components or structures present in the tissue. In such a method, it is preferred that the previous mapping of features is achieved by measuring samples of tissue experimentally.

Alternatively or in addition, it is preferred that the mapping between features of the data and components or structures in the tissue taking the form of a multi dimensional table, with a dimension for each measurable component or structure. A feature of the spectral data may be used to select a sub set of these tables, and one or more features are subsequently used to select further sub sets of tables relating to components or structures within the tissue.

The present invention will now be described in further detail and with reference to the accompanying drawings, in which:—

Figure 8:
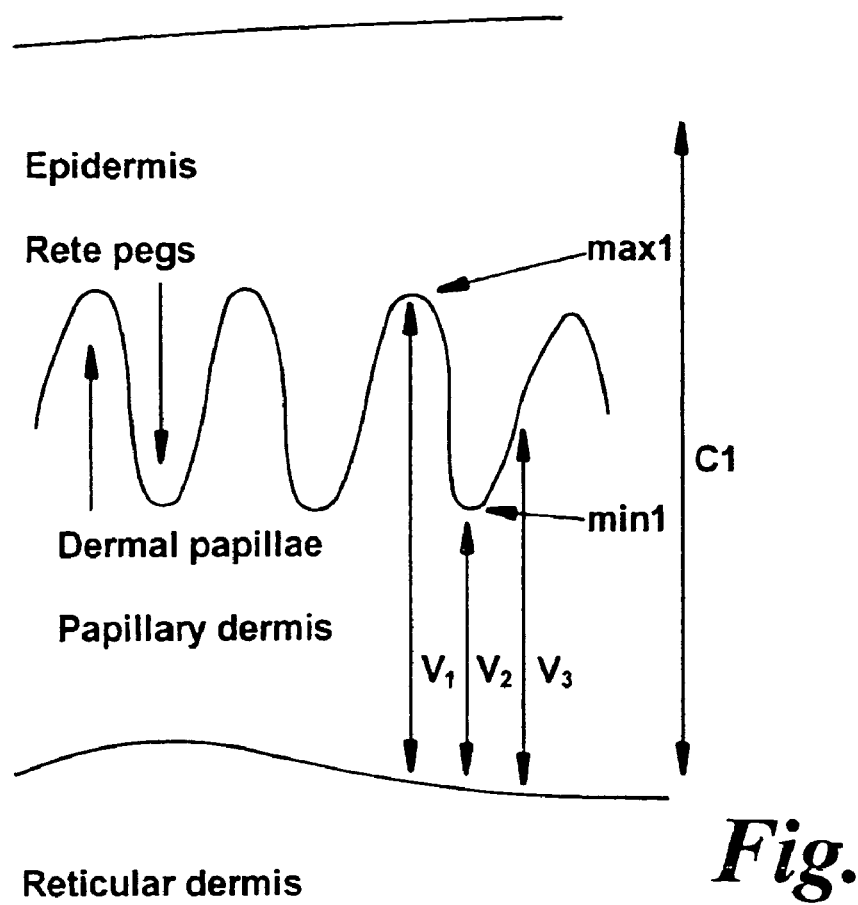
Figure 9:
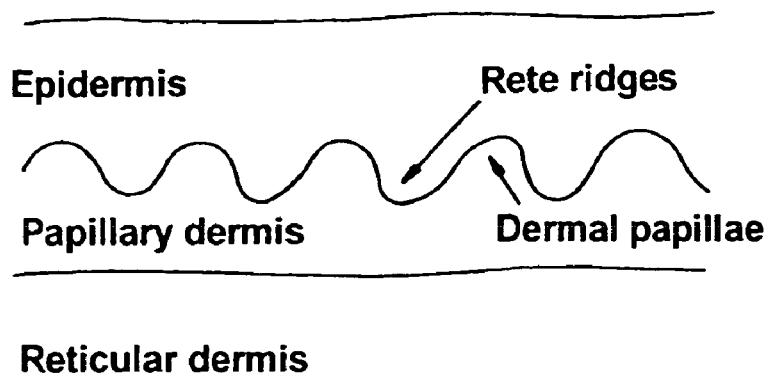
Figure 10:
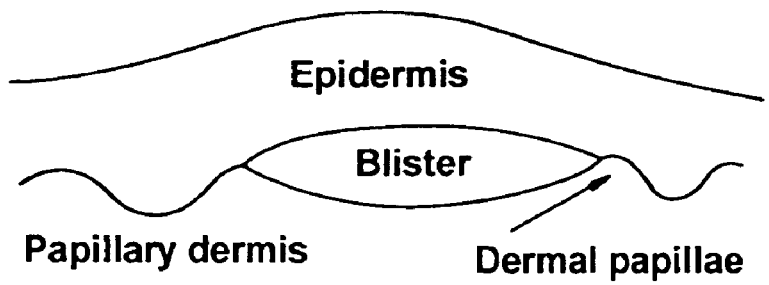
Figure 11:
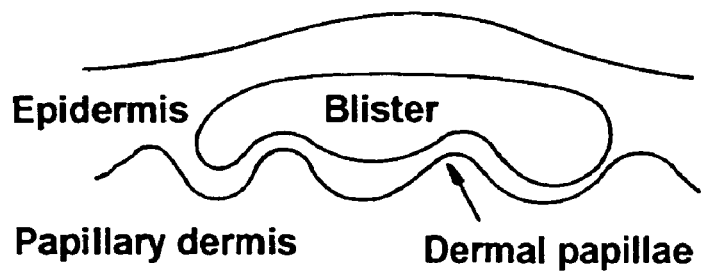
Figure 12:
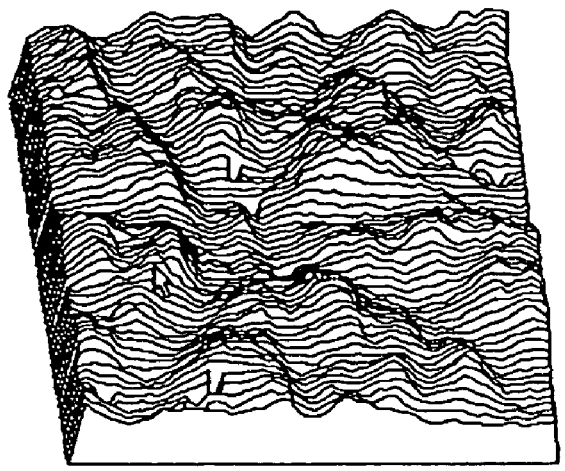
Figure 13:
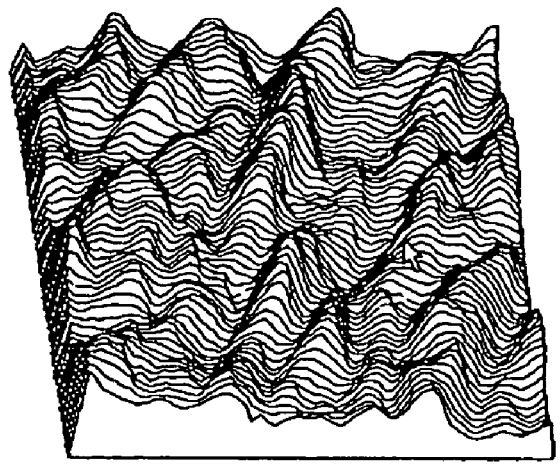
Figure 14:
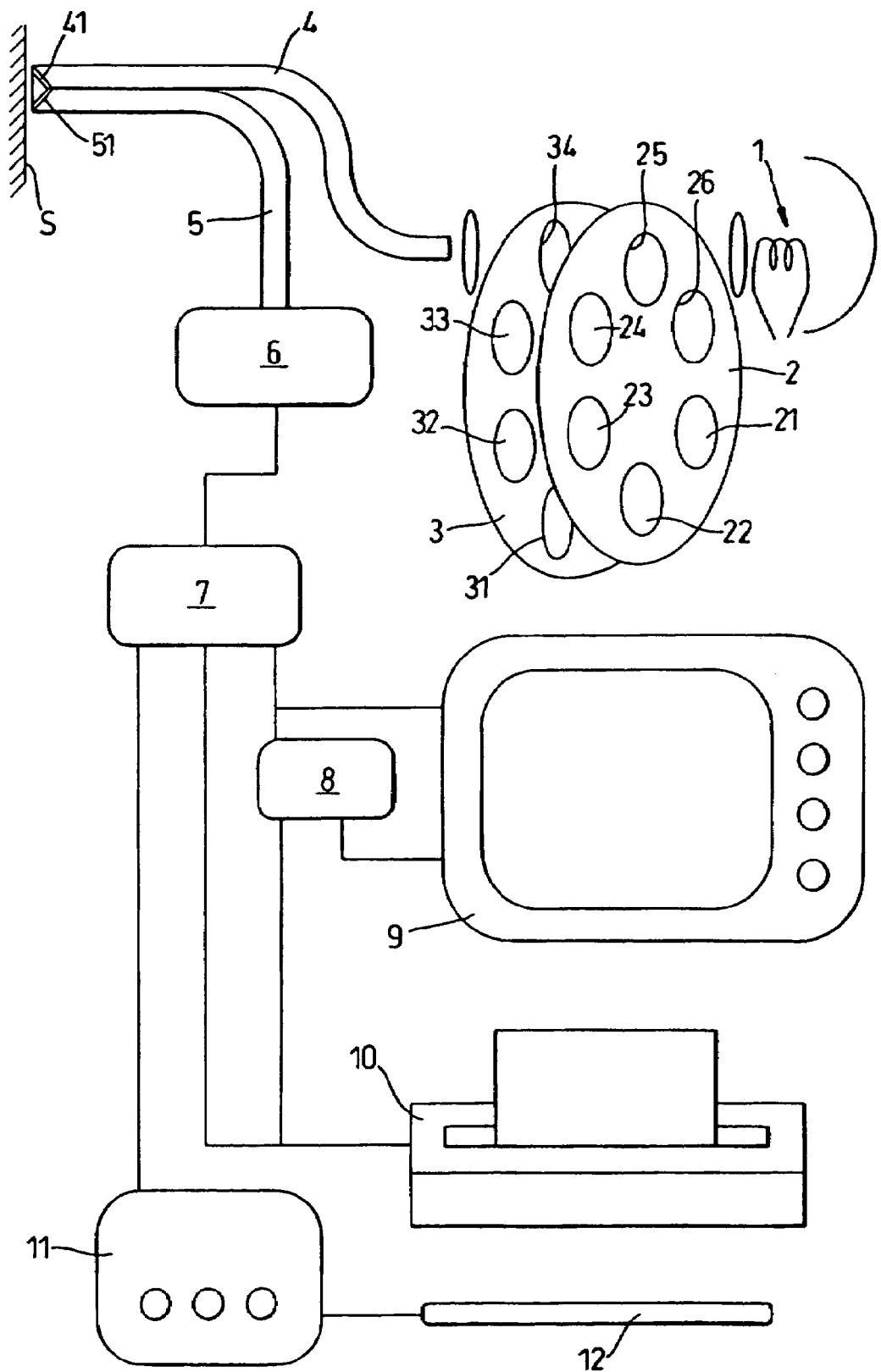
Figure 15:
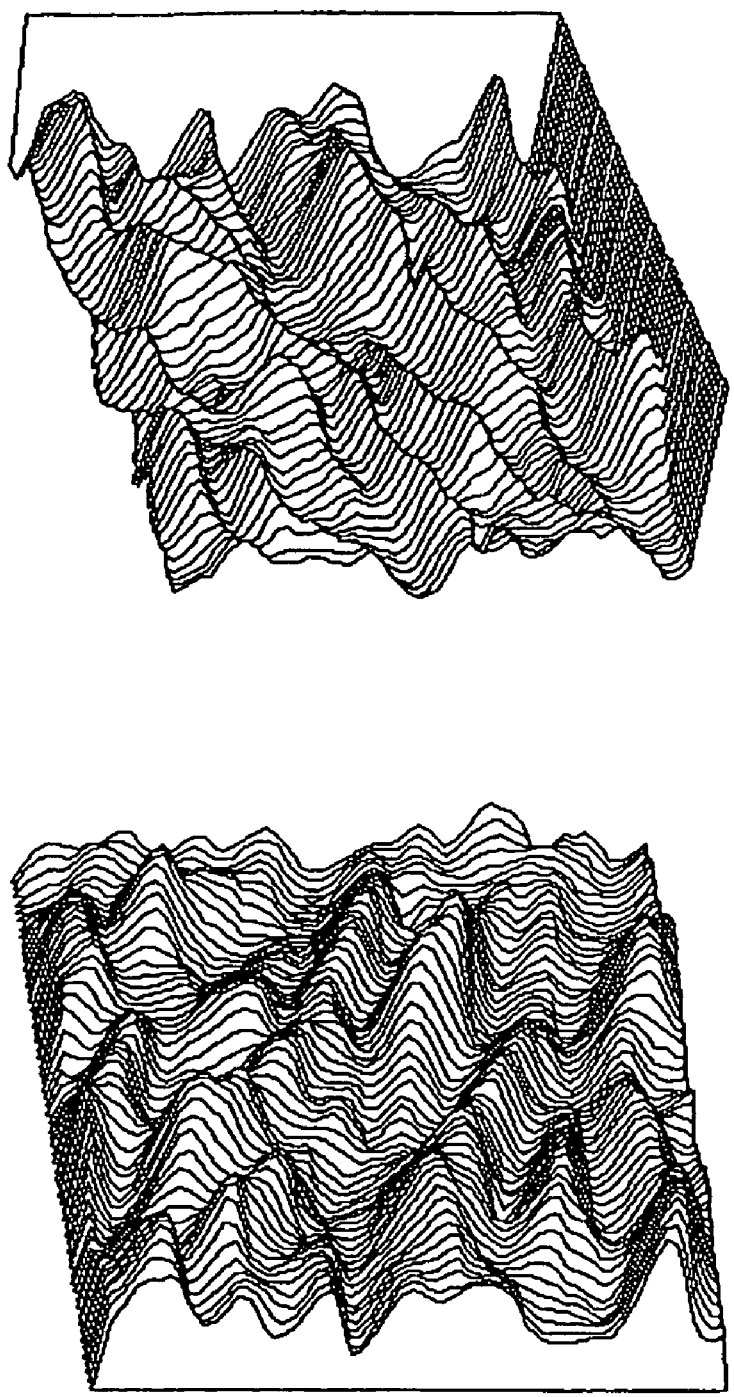

FIG. 8 shows measurements of the dermal papillae and rete ridges, as described hereinabove, FIGS. 9 to 11 are diagrammatic representations of sections through human skin such as may be revealed by conventional biopsy techniques, FIGS. 12 and 13 are representations of the dermo-epidermal boundary such as may be mapped by the present invention FIG. 14 is a schematic diagram of apparatus according to this invention, and, FIG. 15 shows representations of the rete ridges (top) and dermal papillae (bottom) from an area of skin ascertained by using the technique of the present invention.

Figure 16:
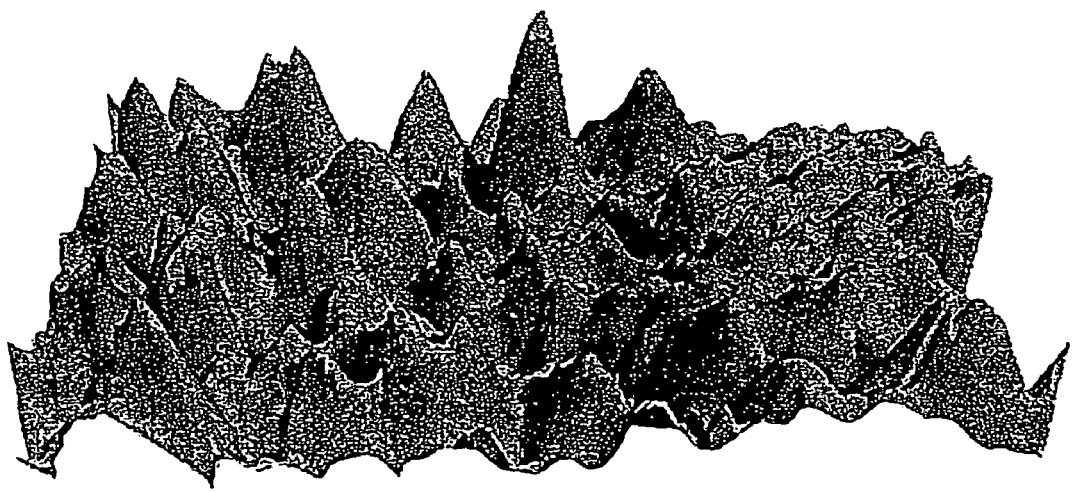

FIG. 16 shows a representation of a basal cell carcinoma ascertained by using the technique of the present invention.

Figure 1:
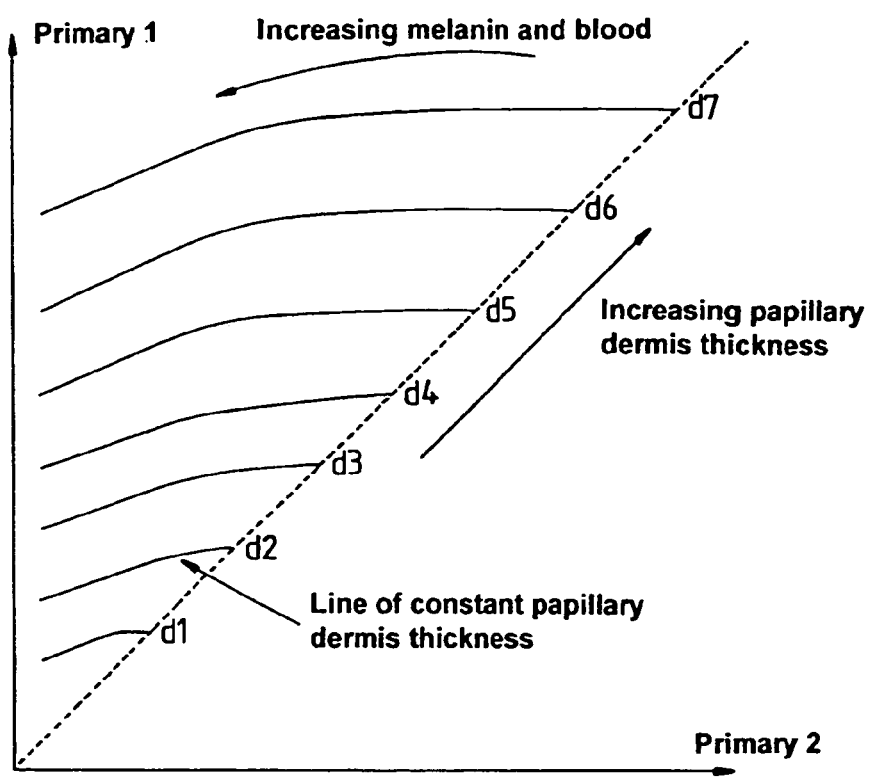
FIG. 1 is a graph showing variation of brightness with papillary dermis thickness for primaries 1 and 2, as described hereinabove.
Figure 2:
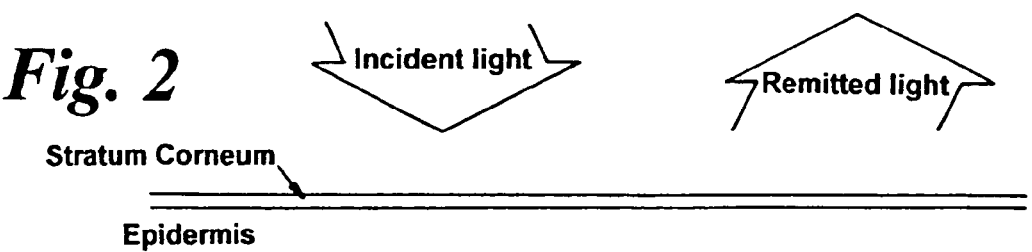
FIG. 2 is a schematic cross-sectional view through a section of skin illustrating melanin descent into the papillary dermis.
Figure 2:
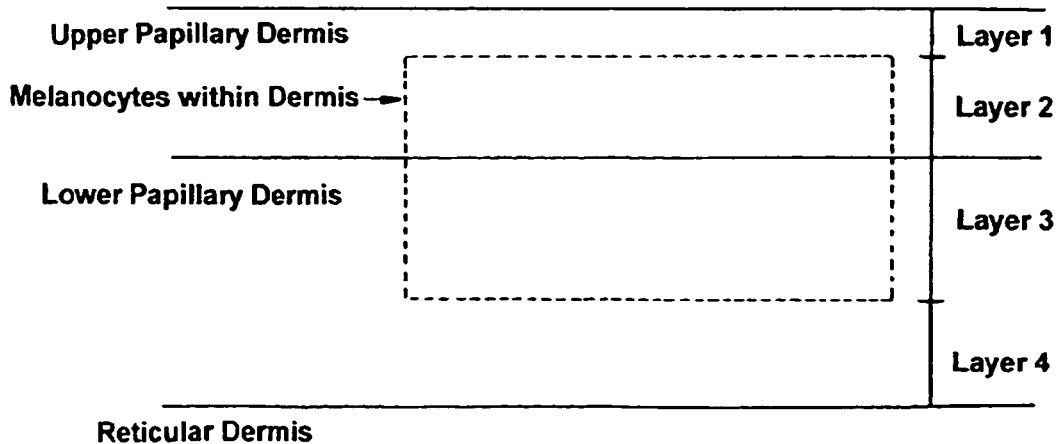

FIGS. 1, 2 and 8 have been mentioned above.

Figure 3:
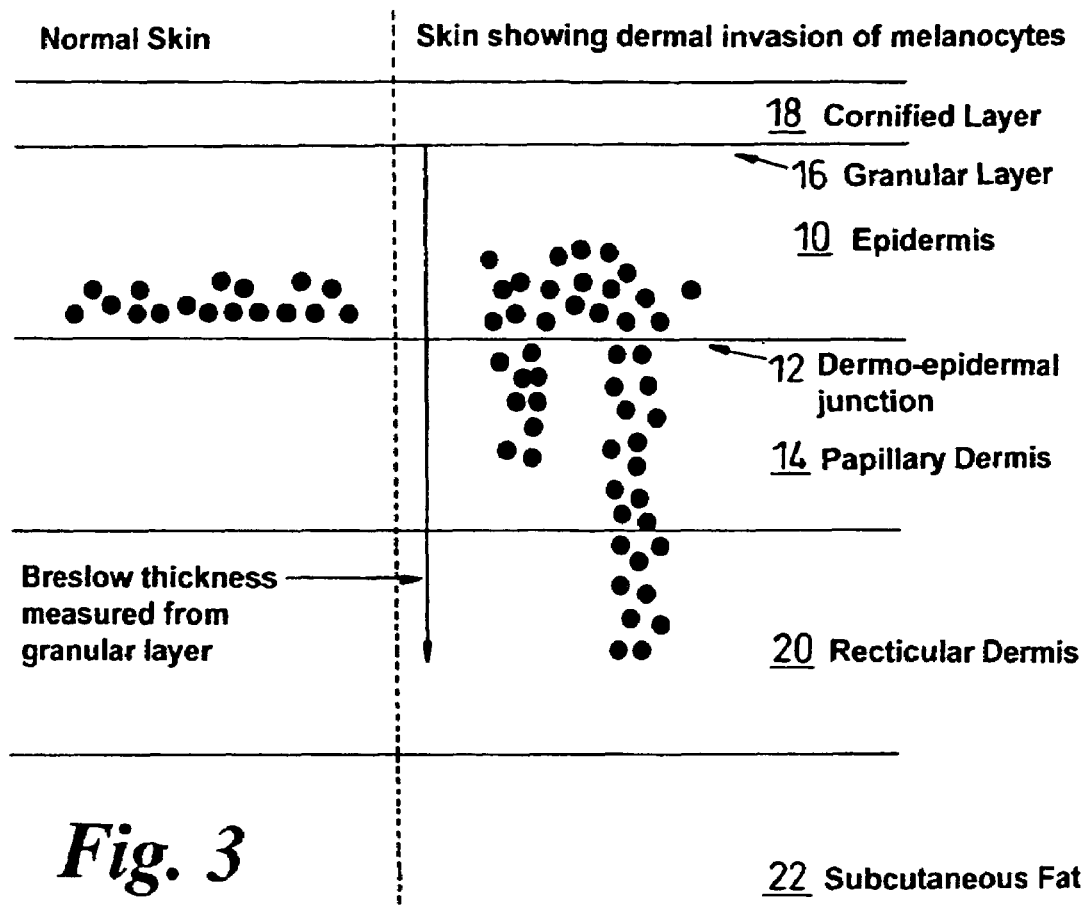
FIG. 3 is a schematic cross-sectional view through a section of skin illustrating normal, healthy regions and an abnormal region where, in this case, melanin descent into the papillary dermis and the reticular dermis has taken place.

Referring now to FIG. 3 of the drawings, a schematic skin section is shown wherein melanin (indicated by the black circles in FIG. 3) in normal healthy skin are present in the lower part of epidermis 10 adjacent but above the dermo-epidermal junction 12 between the epidermis and the papillary dermis 14. The Breslow thickness referred to above is the depth of melanin invasion in millimeters measured from granular layer 16 which is a layer in the epidermis 10 where the skin goes scaly and forms the tough outer cornified layer 18. In the abnormal region of the skin, the melanin is shown as having descended not only into the papillary dermis 14, but also into the underlying reticular dermis 20 lying above the subcutaneous fat layer 22. It is to be appreciated that, in other cases, melanin decent can be into any layer of the skin and may even be into the subcutaneous fat layer 22.

Figure 4:
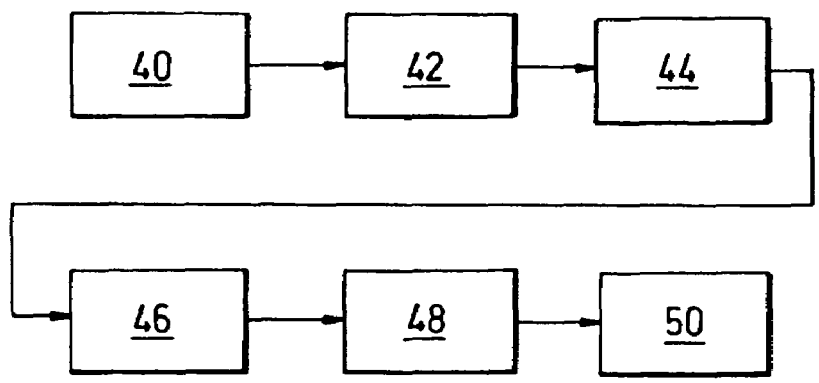
FIG. 4 is a block diagram showing the steps involved in one embodiment of the method of the present invention.

Referring now to FIG. 4, there is shown a block diagram illustrating the steps involved in a typical method of measurement in accordance with the present invention. In FIG. 4, block 38 exemplifies method step (i) above the determination of papillary dermis thickness by shining infrared light at two wavelengths on an area of skin being subjected to measurement and measuring the amount of light reflected from a plurality of points within that area. Block 40 exemplifies method step (ii) above the acquisition of an image at visible wavelengths of the same skin area. This can be by CCD camera, digitized film or any other convenient means. Block 42 exemplifies method step (iii) above the transformation of the image into corrected color space of the skin model at a predetermined papillary dermis thickness. Block 44 exemplifies method steps (iv and v) above—the identification of regions containing dermal melanin, by comparing the corrected skin color co-ordinates with the reference color co-ordinate range. Block 46 exemplifies method step (vi) above—use of the corrected color space to calculate the amounts of epidermal melanin within normal regions adjacent to the regions containing dermal melanin and use thereof to give an indication of the amounts thereof which exist in the regions containing dermal melanin. Block 48 exemplifies a first part of method step (vii) above—calculation of dermal invasion using the measured coloration of the abnormal regions and the calculated amount of epidermal melanin from 46. Block 50 exemplifies a second part of method step (vii) above—transformation of the calculated dermal invasion of melanin into either the Breslow thickness or the Clark's level of invasion. This can be reported as either representing the maximum invasion or as an image showing invasion over the skin.

Figure 5:
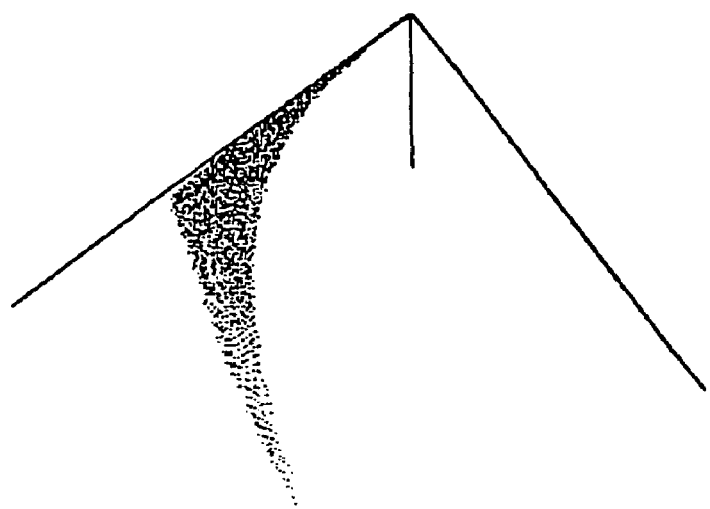
FIG. 5 is a diagram showing the predicted surface of normal skin coloration within a three-dimensional color space.

Referring now to FIG. 5, the shaded surface indicates the range of colorations which can exist in normal healthy skin corrected to the predetermined papillary dermis thickness. Skin colorations which depart from this surface are indicative of dermal melanin.

Figure 6:
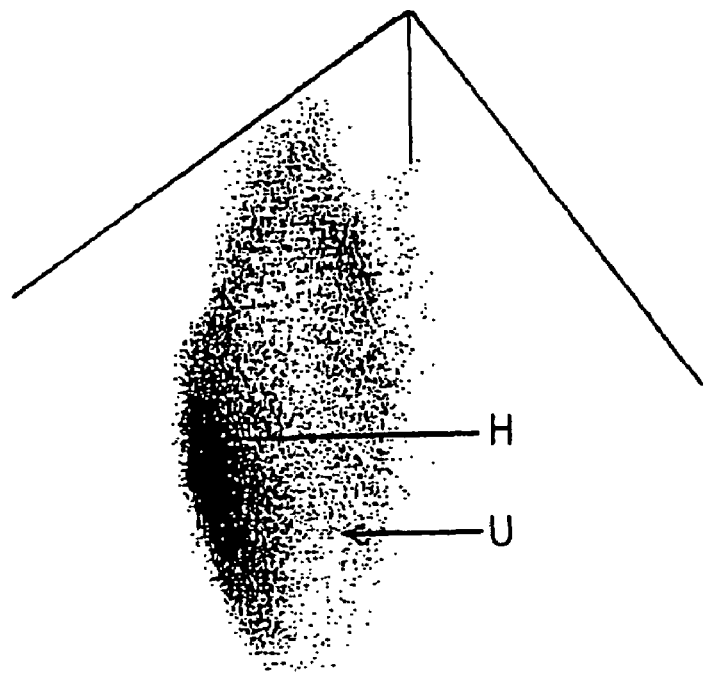
FIG. 6 is a diagram showing coloration within the skin cancer that is shown in FIG. 7 in the same 3-D color space as depicted in FIG. 5, wherein areas of normal and abnormal coloration are shown.
Figure 7:
FIG. 7 is a photographic image of the skin cancer.

Referring now to FIGS. 6 and 7, it can be seen that a region of the skin which is shown in FIG. 7 and which is indicated by arrow H in FIG. 6 lies at a position corresponding to part of the shaded surface illustrated in FIG. 5 and is indicative of normal healthy skin, whereas an adjacent region indicated by arrow U in FIG. 6 lies outside such surface and is indicative of skin containing dermal melanin. Comparison of the coloration of these two adjacent regions H and U enables the depth of melanin invasion in the abnormal region of the skin in FIG. 7 to be computed.

FIG. 9 is an illustration of a section through normal healthy skin showing the epidermis, the papillary dermis and the reticular dermis, and shows the irregular dermo-epidermal boundary formed between the papillary dermis and the epidermis by the interpenetrating dermal papillae and the rete ridges of the epidermis.

FIG. 10 is an illustration of a section through skin showing a blister due to bullous pemphigoid which gives rise to sub-epidermal blistering which distends the local dermo-epidermal boundary architecture.

FIG. 11 is an illustration of a section through skin showing a blister due to *Pemphigus vulgaris* which is located within the thickness of the epidermis and which does not distend the local dermo-epidermal boundary architecture.

FIGS. 12 and 13 are maps of the dermo-epidermal boundary provided by the adoption of one aspect of the present invention, each representing a skin area of about 0.75 mm square.

In both cases the skin is normal. The shallow papillae and rete ridges shown in FIG. 12 indicate that the skin is from an area which is not subject to high stress in the day-to-day life of the subject. It is in fact from the lower back. In FIG. 13, the dermo-epidermal boundary is more sharply corrugated and with a shorter wavelength, indicating a greater stress to that area arising from the day-to-day life of the subject. The FIG. 13 map is of skin from the shoulder. The greater degree of corrugation is associated with a greater need for elasticity and/or a greater need for a resistance to shear between the epidermis and the dermis.

Referring now to FIG. 14, a light source 1 is arranged to direct a beam of light onto a first filter wheel 2 which contains a number of holes 21 to 26 each of which may selectively be brought into the light path. One such hole is left empty for the direct transmission of light from the light source 1, while the remainder contain screens, for example of stainless steel wire gauze which serve as gray-scale filters, cutting down light-transmission without affecting its spectral characteristics. The number of gray-scale filters may be as high or as low as desired. Behind the first filter wheel 2 is a second filter wheel 3 which accommodates a number of color filters. Four such filters 31 to 34 are shown. Again, the number of color filters may be as high or as low as desired. One such filter may be absent for the direct transmission of light.

The color filters would together cover as much of the spectrum as required, for example from the infra red, through to the ultra violet. For the purpose of reliably measuring the concentration of collagen within the papillary dermis, it would be possible to operate at a single wavelength of around 1050 nm, for example using a 10 nm full width-half maximum bandpass filter centered on that wavelength. This is because the absorption of light of that wavelength by melanin is negligible. However, sensors which are capable of operating in that region are expensive and it is preferred to use shorter wavelengths and to take measurements at two different wavelengths where the absorption characteristics of melanin and blood are different so that melanin and blood concentrations can be calculated and/or compensated for. It is in particular preferred to use two 10 nm full width half maximum bandpass filters respectively centered on 694 nm and 940 nm. Other color filters may be used as desired for monitoring particular wavelengths or wavelength bands. A particularly preferred filter set includes five 10 nm full width half maximum bandpass filters respectively centered on 420, 568, 580, 694 and 940 nm, and three broad band (80 nm) filters centered on 450, 550 and 650 nm.

The reason for using gray-scale filters is that a rather high intensity light source is required for obtaining measurements in the infra-red region due to the low transmission of color filters passing light of such wavelengths. In fact we presently prefer to use a xenon light source rated at 300 Watt. Direct transmission of such light, or transmission through for example a yellow filter could burn out a sensor suitable for monitoring in the infra-red. The use of a suitably selected set of gray-scale filters enables a single light source and a single sensor to be used, and this simplifies the apparatus and keeps costs down. A suitable set of gray-scale filters comprises those passing 50%, 10% and 1% of incident light The light is passed to a bundle of optical fibers 4 through which it is transmitted to the skin S of the patient, or even to an appropriate photographic image of that skin, via a polarizing filter 41. Remitted light is carried back through a second polarizing filter 51 and a second bundle of optical fibers 5 to a photo-receptor unit 6. In other embodiments, the optical fibers 4, 5 run along an endoscope appropriate for the in vivo examination of internal epithelial tissue.

The projected light is preferably polarized, and the remitted light is suitably cross-polarized before monitoring. This is especially suitable for monitoring the presence of chromophores beneath the epidermis. Since little scattering of light takes place in the epidermis, any cross-polarized light which is detected must have been remitted from or via the (papillary) dermis, and this allows surface effects and the effects of the epidermis to be eliminated. A similar effect can be achieved without using cross-polarized illumination by coating the surface of the skin with a transparent oil which removes direct reflections at the skin surface.

The two polarizing filters 41, 51 are set so that their respective planes of polarization are at right angles, to eliminate specularly reflected light.

The photo-receptor unit 6, which may simply measure the intensity of the remitted light where a series of color filters is used as illustrated, emits a signal to a comparator 7 which may be constituted as a suitably programmed PC.

As previously mentioned, the photo-receptor is suitably a CCD array, for example a 20×15 mm array adapted to resolve 800×600 pixels.

The use of the bundles of optical fibers adds greatly to the convenience of use of the apparatus since a relatively small unit at the end of a flexible lead may thereby be brought to the patient's skin S: thus the physical posture of the subject during measurement is largely irrelevant and he or she may be made as comfortable as possible.

The comparator 7 is arranged to process the signals received which relate to the intensity of light remitted at the wavelengths 694 nm and 940 nm, and to derive therefrom a signal proportional to the concentration of collagen within the papillary dermis.

The comparator 7 is suitably arranged to supply the results for each pixel monitored via a processor 8 to a display monitor 9 and/or to a printer 10. The processor 8 is arranged to take the signal proportional to the collagen concentration and to use that signal as a measure of altitude to generate a relief map for printing or display. The processor 8 is suitably programmed to allow rotation of the display of the relief map. Examples of such relief maps which show the architecture of the dermo-epidermal boundary constitute FIGS. 4 and 5 of this specification.

The present invention at least in its most preferred embodiments, enables the generation of information regarding a number of features of any skin being examined. To allow an accurate diagnosis of disorders of the skin, or the prognosis of treatment for such disorders, or the monitoring of healthy skin, it is important that the spatial relationship between these features can be understood. Such an understanding of the dermo-epidermal boundary is greatly facilitated by preferred embodiments of the present invention in which such a map is provided. Such a map may be provided within seconds. Previously, examination by biopsy could reveal contours along a single line section, or more than one section if sufficient biopsy material was taken, but it would be at least several hours and could well be several days before the results were available to the clinician.

The comparator 7 may also receive signals relating to the intensity of light remitted in the red, yellow and blue regions of the spectrum, and of remitted white light. The comparator is arranged to assign a notional position in a color space according to co-ordinates represented by these red, yellow and blue values and to note that position having regard to the infra-red value. Instead of measurements over the three primary wavebands, other filters may be provided so that the visible spectrum is split up into four or more wavebands. This establishes four or more co-ordinates, and the comparator may thus assign a notional position in a color space having four or more dimensions. That position can be unique as representing the presence, depth, offset and concentration of any one or more of a range of chromophores within the skin. The comparator is suitably arranged to supply these results to a display monitor 9 and/or to a printer 10, and it may be arranged to pass control signals to the power supply 11 of a medical laser 12 or other source of radiation whether coherent or non-coherent.

The control signal may thus be used for controlling or operating one or more of the following: a display device such as a display monitor, a printer, or a medical laser or other treatment device or apparatus.

The monitor 9 may be and preferably is provided with a touch screen whereby any of the various operational or programming steps may be initiated.

In some preferred embodiments of the invention, a mask is provided to surround the area of skin being illuminated and remit light back to the photoreceptor 6. The incorporation of a standard reflector into such a mask simplifies calibration of the apparatus.

Thus by making use of the invention it is possible to obtain images which correspond to: (a) the visual appearance of the skin surface; (b) the architecture of the dermo-epidermal boundary; and (c) the presence of any chromophore within the skin, including its depth and concentration, and an indication of its nature.

To facilitate the spatial correlation of two or more of such images, for example one showing the appearance of the skin and another showing a particular feature, or of two images showing different features, we have developed a technique whereby a further image is generated. Thus we also provide a method of and apparatus for showing both images together with the proportion or intensity of each adjusted through the use of a control of some means and this allows spatial correlation of the input images. For example the two original images might be supplied in overlapping relation to a monitor screen of a PC, and the two images be relatively faded in and faded out in order to change from viewing one image to another. This allows correlation between the surface appearance of skin and any underlying feature which might have given rise to that appearance. It is of particular interest in the examination of any lesion in the skin.

The display first shows an image, which may or may not be magnified, of the lesion as it actually appears to the eye or a surface microscopy view or an image taken using cross polarized illumination or an image showing a particular feature. By selecting a particular feature such as blood or areas of melanin invasion into the dermis or melanin within the epidermis etc. the display can then be faded to show this feature as an image. The fading allows a progression, or mixing, between the two views and is a convenient means of allowing a spatial correlation to be made between the features and the lesion image.

The images may be images representing the presence of particular existing features of the skin or one or more of them may be computer generated images representing the predicted effects of a treatment such as a laser irradiation treatment. For example, as mentioned above, it is possible to generate a color representation of the expected result of a laser irradiation treatment, and it would be possible to generate one such image for each of a set of different irradiation intensities. This would enable a comparison of the different courses of treatment and would allow selection of an appropriate treatment, for example the one giving the most cosmetically acceptable result.

The analysis afforded by the present invention is also of value in the selection of the wavelength or wavelengths of any light (infra-red, visible or ultra-violet) irradiation treatment that may be indicated. For example, a knowledge of the constituents of a lesion allows a selection of a wavelength of light radiation which will be most strongly and preferentially absorbed by constituents of that lesion. Also, a knowledge of the existence and structure and composition of overlying tissue (including any discontinuities which it might contain) allows the most favorable compromise to be reached between low absorption in the overlying tissue and high absorption in the lesion to be destroyed, thus providing the most effective treatment with the lowest radiation dosage. Thus a laser of an appropriate wavelength may be selected, and/or a variable wavelength laser may be tuned, or an appropriate filter set may be used in conjunction with a source of non-coherent radiation.

FIG. 15 shows a map of rete ridges above corresponding dermal papillae derived using this invention.

As illustrated by FIG. 16, the dermo-epidermal boundary architecture is important inter alia for assessing the extent of basal cell carcinomas. FIG. 16 is a map of the dermo-epidermal boundary which includes a part affected by such a carcinoma. The contrast between well developed and distinct papillae of healthy skin to the left of the Figure and the area of almost destroyed papillae at the upper right section of the Figure is well marked and clearly shows the boundary of such a carcinoma. The information imparted by such a map of the dermo-epidermal boundary is plainly of value in assisting diagnosis and in the planning of surgical excision boundaries.

The invention claimed is:

1. Apparatus for monitoring the presence of individual chromophores in a tissue sample, said apparatus comprising:
   a light source configured to illuminate an area of a tissue sample with different wavelengths of light;
   a photo-receptor configured to receive light re-emitted by an area of a tissue sample illuminated by said light source; and
   a spectroscopic analyzer configured to utilize the spectral characteristics of re-emitted light received by said photo-receptor and the spectral characteristics of light projected by said light source to identify the presence of said one or more chromophores within the area of the illuminated tissue sample from which re-emitted light is received by said photo-receptor, wherein said spectroscopic analyzer comprises:
   records of the spectral characteristics of light re-emitted by reference samples of known structure containing identified chromophores;
   said spectroscopic analyzer being configured to compare the spectral characteristics of re-emitted light received by said photo-receptor with said records to identify the record including spectral characteristics most closely matching the characteristics of said re-emitted light received by said photo-receptor and to output as an identification of individual chromophores present in the area of the illuminated tissue sample from which re-emitted light is received by said photo-receptor an identification of the chromophores associated with said spectral characteristics by said record.

2. Apparatus in accordance with claim 1, wherein said records comprise records of the spectral characteristics of light remitted by reference samples of epithelial or epithelial and sub-epithelial tissue.

3. Apparatus in accordance with claim 2, wherein said records comprise records of the spectral characteristics of light remitted by reference samples of skin.

4. Apparatus in accordance with claim 1, wherein said records comprise records of the spectral characteristics of light remitted by reference samples of normal healthy tissue.

5. Apparatus in accordance with claim 1, wherein said records comprise records of calculated estimated spectral characteristics of light re-emitted by samples of tissue of known structure containing identified chromophores.

6. Apparatus in accordance with claim 1 wherein said light source is operable to selectively illuminate an area of a tissue sample with different wavelengths of light.

7. Apparatus in accordance with claim 6, wherein said light source further comprises a set of filters for selective substitution into the tissue-incident light path in order to selectively illuminate an area of tissue with different wavelengths of light.

8. Apparatus in accordance with claim 1, wherein said light source further comprises a polarizing filter arranged to polarize the light which illuminates said area of tissue.

9. Apparatus in accordance with claim 8, further comprising a cross-polarizing filter arranged to cross-polarize light remitted from said area of tissue before it is received by said photo-receptor.

10. Apparatus in accordance with claim 1, wherein said light source is operable to illuminate said area of tissue with light having a wavelength in excess of 600 nm.

11. Apparatus in accordance with claim 1, wherein said photo-receptor is operable to detect re-emitted light having wavelengths in the 800 to 1000 nm band and the 600 to 800 nm band.

12. Apparatus in accordance with claim 1, wherein said photo-receptor is operable to receive light remitted from an array of points and said spectroscopic analyzer is operable to identify the presence of one or more individual chromophores at each of said points in said array.

13. Apparatus in accordance with claim 12, wherein said photo-receptor is operable to receive light remitted from points with a resolution of at least 20 lines or dots per mm.

14. Apparatus in accordance with claim 1 wherein said spectroscopic analyzer is operable to determine on the basis of the spectral characteristics of said received re-emitted light the depth of papillary dermis of a tissue sample being monitored and to identify the presence of said one or more individual chromophores within the area of the illuminated issue sample from which re-emitted light is received by said photo-receptor utilizing the spectral characteristics of said received re-emitted light and said determined depth of papillary dermis.

15. Apparatus in accordance with claim 1 wherein said light source, photo-receptor and spectroscopic analyzer are together adapted to generate a signal indicative of the presence of chromophores which is substantially independent to the variation of spectral characteristics of re-emitted light arising due to the presence of a predetermined chromophore.

16. Apparatus in accordance with claim 15 wherein said light source and photo-receptor are arranged to project and detect light at wavelengths which are substantially unaffected by the presence of a predetermined chromophore.

17. Apparatus in accordance with claim 15 wherein said spectroscopic analyzer is arranged to process data indicative of the spectral characteristics of re-emitted light received by said photo-receptor to generate signals which are indicative of the presence of chromophores which are substantially independent of the variation in spectral characteristics arising due to the presence of a predetermined chromophore.

18. Apparatus in accordance with claim 15, wherein said light source and photo-receptor are arranged to project and detect light at wavelengths which are substantially unaffected by the presence of a predetermined chromophore, and wherein said predetermined chromophore comprises a chromophore selected from the group consisting of melanin, blood and tattoo pigments.

19. Apparatus according to claim 1, further comprising a light guide of which a least part is flexible provided for conducting light between said light source, said tissue sample and said photo-receptor.

20. Apparatus according to claim 19, wherein said light guide comprises an endoscope.

21. Apparatus according to claim 19, wherein said light guide terminates in a head adapted for placing against an area of skin.

22. Apparatus according to claim 1, wherein said light source is operable to vary the size of the area of tissue from which re-emitted light is received.

23. Apparatus in accordance with claim 1, wherein said light source is operable to project light which either has a wavelength sufficiently far into the infra-red that its absorption by melanin and blood is negligible, or which has at least two wavelengths of which at least one is in excess of 600 nm, wherein said spectroscopic analyzer is operable to process data indicative of the spectral characteristics of re-emitted light received by said photo receiver to determine variations in spectral characteristics arising independently of variations due to the presence of melanin and blood and to utilize said determined independent variations in spectral characteristics to generate a signal indicative of the concentration of collagen within the papillary dermis of a tissue sample being monitored.

24. Apparatus in accordance with claim 1 further comprising a signal generator operable to generate control signals on the basis of the determination of the presence of one or more chromophores in a tissue sample by said spectroscopic analyzer, wherein said control signals are operable to control an apparatus selected from a display monitor, a printer, a medical laser and a treatment device.

25. A method of monitoring the presence of individual chromophores in a tissue sample, comprising:
    illuminating an area of a tissue sample with different wavelengths of light using a light source;
    receiving light re-emitted by an area of a tissue sample illuminated by said light source with a photo-receptor; and
    operating a spectroscopic analyzer to utilize the spectral characteristics of re-emitted light received by said photo-receptor and the spectral characteristics of light projected by said light source to identify the presence of said chromophores within the area of the illuminated tissue sample from which re-emitted light is received by said photo-receptor, the operating of said spectroscopic analyzer including:
        recording the spectral characteristics of light re-emitted by reference samples of tissue of known structure containing identified chromophores, and
        arranging said spectroscopic analyzer to compare the spectral characteristics of re-emitted light received by said photo-receptor with said records to identify the record including spectral characteristics most closely matching the characteristics of said re-emitted light received by said photo-receptor and to output as an identification of individual chromophores present in the area of the illuminated tissue sample from which re-emitted light is received by said photo-receptor an identification of the chromophores associated with said spectral characteristics by said record; and
    deriving data relating to the presence, depth, and concentration of chromophores and creating and displaying a map thereof.

26. The method according to claim 25, further comprising
    deriving data relating to the presence, depth, and concentration of any chromophore selected from the group consisting of: melanin, blood, hemoglobin, oxy-hemoglobin, bilirubin, tattoo pigments or dyestuffs, keratin, collagen and hair.

27. The method according to claim 25, further comprising mapping the extent of a basal cell carcinoma.

28. A method of monitoring the presence of individual chromophores in a sample of tissue, comprising:
    storing records of the spectral characteristics of light re-emitted by reference samples of tissue of known structure containing identified chromophores;
    illuminating an area of a tissue sample with different wavelengths of light using a light source;
    receiving light re-emitted by the illuminated area of tissue at a photo-receptor;
    comparing the spectral characteristics of re-emitted light received by said photo-receptor with said records to identify the record including spectral characteristics most closely matching the characteristics of said re-emitted light received by said photo-receptor; and
    outputting as an identification of the individual chromophores present in the area of the illuminated tissue sample from which re-emitted light is received by said photo-receptor an identification of the chromophores associated with said spectral characteristics by said record.

29. A method according to claim 28, wherein the storing of the records includes storing records of the spectral characteristics of light remitted by reference samples of epithelial or epithelial and sub-epithelial tissue.

30. A method according to claim 29, wherein the storing of the records includes storing records of the spectral characteristics of light remitted by reference samples of skin.

31. A method according to claim 28, wherein the storing of the records includes storing records of the spectral characteristics of light remitted by reference samples of normal healthy tissue.

32. A method according to claim 28, wherein the storing of the records includes storing records of calculated estimated spectral characteristics of light re-emitted by samples of tissue containing identified chromophores.

33. A method according to claim 28, further comprising the steps of: deriving data relating to the presence, depth, and concentration of chromophores; and creating and displaying a map thereof.

34. A method according to claim 28, comprising: deriving data relating to the presence, depth, and concentration of any chromophore selected from the group consisting of: melanin, blood, hemoglobin, oxy-hemoglobin, bilirubin, tattoo pigments or dyestuffs, keratin, collagen and hair.

35. A method according to claim 28 which further comprising: passing projected light and/or the remitted light through one or more filters and spectroscopically analyzing the remitted light such that the result of the analysis is independent of the presence of a predetermined chromophore in the tissue.

36. A method according to claim 35 wherein said light source and photo-receptor are arranged to project and detect light at wavelengths which are substantially unaffected by the presence of said predetermined chromophore.

37. A method according to claim 35 further comprising:
    processing data indicative of the spectral characteristics of re-emitted light received by said photo-receptor to generate signals which are indicative of the presence of chromophores which are substantially independent of the variation in spectral characteristics arising due to the presence of said predetermined chromophores; and comparing said processed data with said records to identify the record having the most closely corresponding spectral data.

38. A method according to claim 35 wherein said predetermined chromophore comprises a chromophore selected from the group consisting of melanin, blood and tattoo pigments.

39. A method according to claim 28, further comprising:
determining the depth of papillary dermis of a tissue sample being monitored on the basis of the spectral characteristics of said received re-emitted light; and identifying the presence of individual chromophores within the area of the illuminated issue sample from which re-emitted light is received utilizing the spectral characteristics of said received re-emitted light and said determined depth of papillary dermis.

* * * * *